(12) United States Patent
Berman et al.

(10) Patent No.: US 9,714,985 B2
(45) Date of Patent: Jul. 25, 2017

(54) CALIBRATION ASSEMBLY FOR AIDE IN DETECTION OF ANALYTES WITH ELECTROMAGNETIC READ-WRITE HEADS

(71) Applicant: GLOBALFOUNDRIES U.S. 2 LLC, Hopewell Junction, NY (US)

(72) Inventors: David Berman, San Jose, CA (US); Dylan J. Boday, Tucson, AZ (US); Icko E. T. Iben, Santa Clara, CA (US); Wayne I. Imaino, San Jose, CA (US); Stephen L. Schwartz, Tucson, AZ (US); Anna W. Topol, Jefferson Valley, NY (US); Daniel J. Winarski, Tucson, AZ (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 395 days.

(21) Appl. No.: 14/569,350

(22) Filed: Dec. 12, 2014

(65) Prior Publication Data

US 2015/0097576 A1    Apr. 9, 2015

Related U.S. Application Data

(62) Division of application No. 13/099,358, filed on May 3, 2011, now Pat. No. 9,040,311.

(51) Int. Cl.
*G01R 35/00* (2006.01)
*G01R 33/00* (2006.01)
(Continued)

(52) U.S. Cl.
CPC ......... *G01R 33/0035* (2013.01); *G01N 27/72* (2013.01); *G01R 33/09* (2013.01);
(Continued)

(58) Field of Classification Search
CPC ...... G01R 35/005; G01R 35/00; G01N 31/22; G01N 31/00
(Continued)

(56) References Cited

U.S. PATENT DOCUMENTS 3,823,276 A    7/1974    Maslowski et al.
4,062,047 A    12/1977    Scull
(Continued)

FOREIGN PATENT DOCUMENTS

CN    1454851 A    11/2003
CN    1783219 A    6/2006
(Continued)

OTHER PUBLICATIONS

Office Action from Chinese Patent Application No. 201180060053.7, dated Jun. 27, 2014.
(Continued)

*Primary Examiner* — Christine T Mui

(57) ABSTRACT

According to one embodiment, a calibration assembly includes an outer layer having at least one calibration trench extending along a y-axis, and an encapsulation layer within the calibration trench. The encapsulation layer has a plurality of nanoparticles spaced apart along said y-axis of said at least one calibration trench. Each of said plurality of nanoparticles are provided at known y-axis locations in said calibration trench, and each of the plurality of nanoparticles have a known magnetic property.

15 Claims, 15 Drawing Sheets

(51) Int. Cl.
*G01R 33/12* (2006.01)
*G01N 27/72* (2006.01)
*G01R 33/09* (2006.01)
*G01N 27/74* (2006.01)

(52) U.S. Cl.
CPC ......... *G01R 33/1269* (2013.01); *G01R 35/00* (2013.01); *G01R 35/005* (2013.01); *G01N 27/745* (2013.01)

(58) Field of Classification Search
USPC ................. 436/80; 304/60; 324/600, 601
See application file for complete search history.

(56) References Cited

U.S. PATENT DOCUMENTS

| | | | |
|---|---|---|---|
| 5,005,096 A | 4/1991 | Krounbi et al. | |
| 5,206,590 A | 4/1993 | Dieny et al. | |
| 5,331,493 A * | 7/1994 | Schwarz | G11B 5/3103 360/316 |
| 5,452,164 A | 9/1995 | Cole et al. | |
| 5,465,185 A | 11/1995 | Heim et al. | |
| 5,615,065 A | 3/1997 | Cheung | |
| 5,689,384 A | 11/1997 | Albrecht et al. | |
| 5,764,567 A | 6/1998 | Parkin | |
| 5,922,537 A | 7/1999 | Ewart et al. | |
| 6,027,946 A | 2/2000 | Weitschies et al. | |
| 6,282,051 B1 | 8/2001 | Albrecht et al. | |
| 6,320,719 B1 | 11/2001 | Albrecht et al. | |
| 6,432,346 B1 | 8/2002 | Hall | |
| 6,736,978 B1 | 5/2004 | Porter et al. | |
| 6,770,489 B1 | 8/2004 | Enpuku | |
| 6,962,685 B2 | 11/2005 | Sun | |
| 7,153,366 B1 | 12/2006 | Chen et al. | |
| 7,468,271 B2 | 12/2008 | Golovchenko et al. | |
| 7,556,863 B2 | 7/2009 | Berning et al. | |
| 7,639,448 B2 | 12/2009 | Haustein et al. | |
| 7,639,488 B2 | 12/2009 | Tu | |
| 8,440,093 B1 | 5/2013 | Nassef et al. | |
| 8,525,129 B2 | 9/2013 | Offermans et al. | |
| 8,694,280 B2 | 4/2014 | Awezec et al. | |
| 8,855,957 B2 | 10/2014 | Berman et al. | |
| 2002/0001960 A1 | 1/2002 | Wu et al. | |
| 2002/0119470 A1 | 8/2002 | Nerenberg et al. | |
| 2003/0077616 A1 | 4/2003 | Lomas | |
| 2003/0077642 A1 | 4/2003 | Fritsch et al. | |
| 2004/0219361 A1 | 11/2004 | Cui et al. | |
| 2005/0087000 A1 | 4/2005 | Coehoorn et al. | |
| 2005/0100930 A1 | 5/2005 | Wang et al. | |
| 2006/0128035 A1 | 6/2006 | Coehoorn et al. | |
| 2007/0146715 A1 | 6/2007 | Potyrailo et al. | |
| 2008/0012119 A1 | 1/2008 | Otremba et al. | |
| 2008/0036450 A1 | 2/2008 | Kahlman et al. | |
| 2008/0186023 A1 | 8/2008 | Biziere et al. | |
| 2008/0206104 A1 | 8/2008 | Prins et al. | |
| 2009/0047520 A1 | 2/2009 | Lee et al. | |
| 2009/0072815 A1 | 3/2009 | Kahlman et al. | |
| 2009/0104707 A1 | 4/2009 | Wang et al. | |
| 2009/0152657 A1 | 6/2009 | Suh et al. | |
| 2009/0212768 A1 | 8/2009 | Llandro et al. | |
| 2009/0243594 A1 | 10/2009 | Kahlman | |
| 2009/0268325 A1 | 10/2009 | Iben et al. | |
| 2009/0314066 A1 | 12/2009 | Nieuwenhuis et al. | |
| 2010/0005896 A1 | 1/2010 | Miller et al. | |
| 2010/0017922 A1 | 1/2010 | Shin et al. | |
| 2010/0021708 A1 | 1/2010 | Kong et al. | |
| 2010/0093119 A1 | 4/2010 | Shimizu | |
| 2011/0076670 A1 | 3/2011 | Boday et al. | |
| 2011/0076782 A1 | 3/2011 | Awezec et al. | |
| 2011/0077869 A1 | 3/2011 | Boday et al. | |
| 2011/0077902 A1 | 3/2011 | Awezec et al. | |
| 2012/0157330 A1 | 6/2012 | Boday et al. | |
| 2012/0280675 A1 | 11/2012 | Berman et al. | |
| 2012/0283976 A1 | 11/2012 | Berman et al. | |

FOREIGN PATENT DOCUMENTS

| | | |
|---|---|---|
| CN | 1967660 A | 5/2007 |
| CN | 101509919 A | 8/2009 |
| CN | 101632018 A | 1/2010 |
| EP | 2073016 A1 | 6/2009 |
| WO | 2006047840 A1 | 5/2006 |
| WO | 2008102218 A1 | 8/2008 |
| WO | 2009083856 A2 | 7/2009 |
| WO | 2009157739 A2 | 12/2009 |

OTHER PUBLICATIONS

Notice of Allowance from U.S. Appl. No. 13/099,360, dated Jun. 4, 2014.
Final Office Action from U.S. Appl. No. 13/099,360, dated Feb. 25, 2014.
Non-Final Office Action from U.S. Appl. No. 13/099,360, dated Oct. 1, 2013.
Final Office Action from U.S. Appl. No. 12/970,837, dated Nov. 22, 2013.
Non-Final Office Action from U.S. Appl. No. 12/970,837, dated May 10, 2013.
Restriction Requirement from U.S. Appl. No. 12/970,837, dated Jan. 29, 2013.
Notice of Allowance from U.S. Appl. No. 13/099,358, dated Sep. 15, 2014.
Restriction Requirement from U.S. Appl. No. 13/099,358, dated Jun. 20, 2014.
Piedade, M. et al., "A New Hand-held Microsystem Architecture for Biological Analysis," IEEE Transactions on Circuits and Systems I: Regular Papers, vol. 53, No. 11, Nov. 2006, pp. 2384-2395.
Shen, W. et al., "Detection of DNA labeled with magnetic nanoparticles using MgO-based magnetic tunnel junction sensors," Journal of Applied Physics, vol. 103, 2008, pp. 07A306/1-07A306/3.
Osterfeld, S.J. et al., "Multiplex protein assays based on real-time magnetic nanotag sensing," PNAS, vol. 105, No. 52, Dec. 30, 2008, pp. 20637-20640.
Liandro, J. et al., "Magnetic biosensor technologies for medical applications: a review," Med. and Biol. Eng. and Computing, Springer Berlin, online Jun. 24, 2010, pp. 1-22.
Yammamoto, T. et al., "Active immobilization of biomolecules on a hybrid three-dimensional nanoelectrode by dielectrophoresis for single-biomolecule study," Nanotechnology, 495503, vol. 18, 2007, pp. 1-7.
U.S. Appl. No. 61/246,329, filed Sep. 28, 2009.
Liu et al., "Discrimination of specific and non-specific bindings by dielectrophoretic repulsion in on-chip magnetic bioassays," Biosensors and Bioelectronics 24, 2009, pp. 2294-2297.
Millen et al., "Giant Magenetoresistive Sensors. 2. Detection of Biorecognition Events at Self-Referencing and Magnetically Tagged Arrays," Analytical Chemistry, vol. 80, No. 21, Nov. 1, 2008, pp. 7940-7946.
Nordling, J. et al., "Giant Magnetoresistance Sensors. 1. Internally Calibrated Readout of Scanned Magnetic Arrays," Analytical Chemistry, vol. 80, No. 21, Nov. 1, 2008, pp. 7930-7939.
Statement of Relevance of Non-Translated Foreign Document—WO2009157739.
U.S. Appl. No. 14/498,982, filed Sep. 26, 2014.
Notice of Allowance Communication, U.S. Appl. No. 14/569,376, David Berman et al., Dated May 10, 2016, pp. 1-19.

* cited by examiner

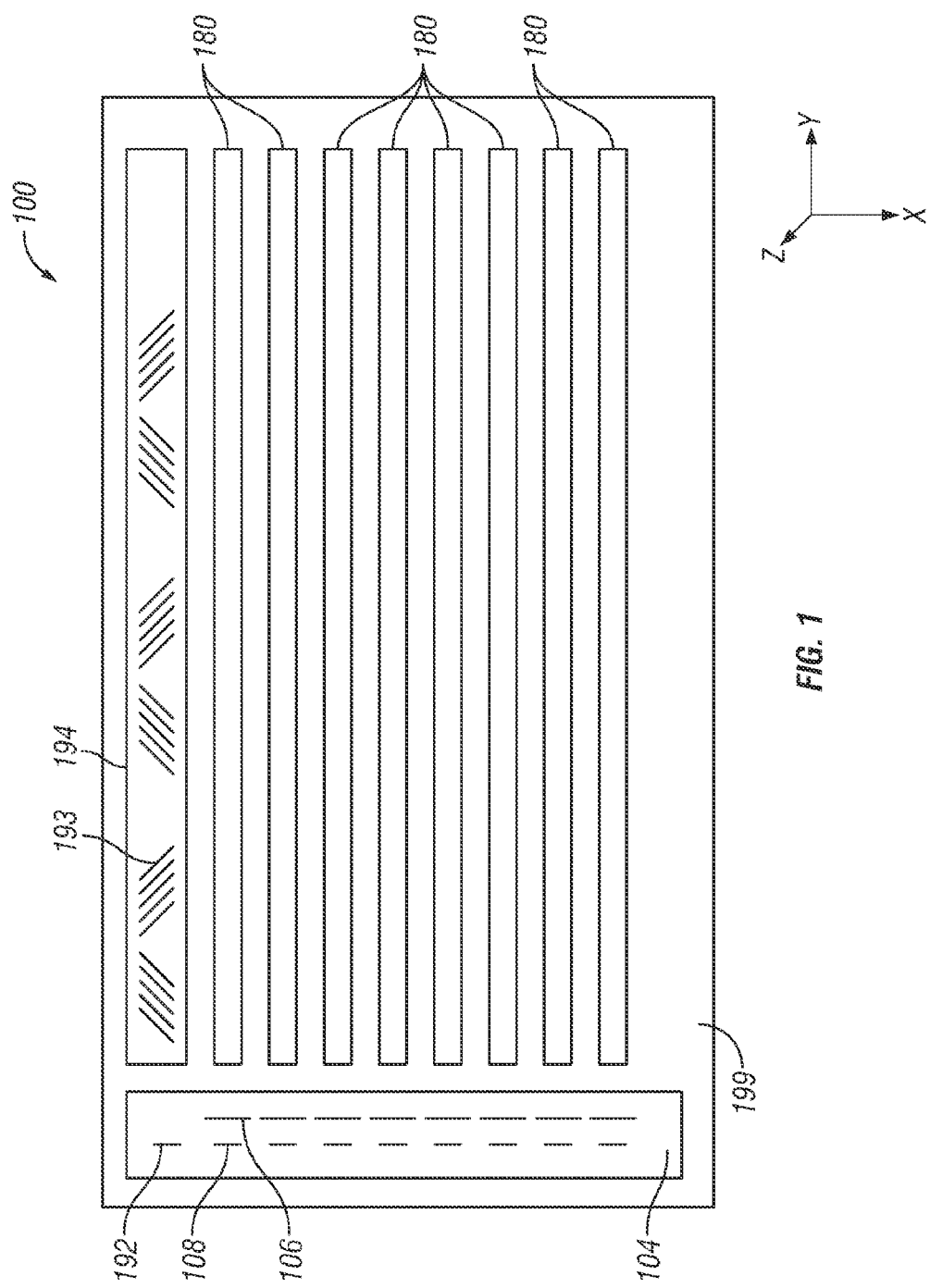

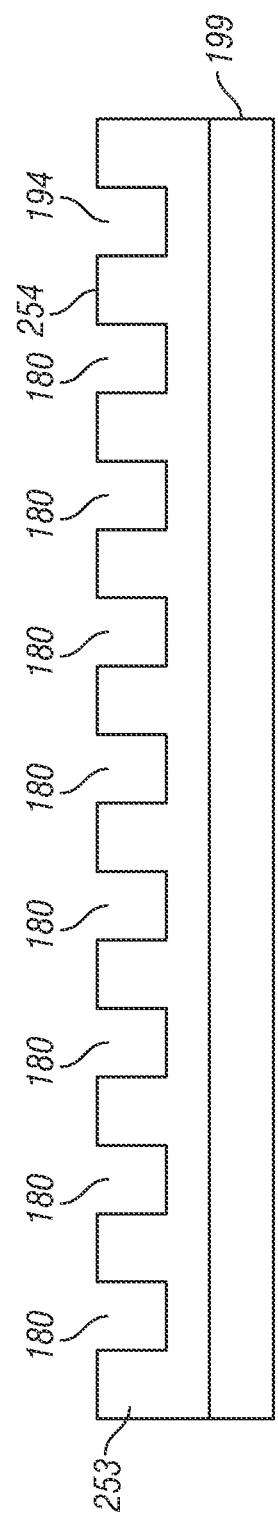
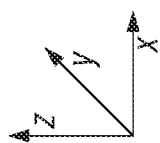
FIG. 2C

CALIBRATION ASSEMBLY FOR AIDE IN DETECTION OF ANALYTES WITH ELECTROMAGNETIC READ-WRITE HEADS

RELATED APPLICATIONS

This application is a divisional of U.S. patent application Ser. No. 13/099,358, filed May 3, 2011, and which is herein incorporated by reference.

FIELD OF THE INVENTION

The present invention relates to devices and processes that incorporate electromagnetic write-heads and magneto-resistive read sensors to detect magnetized nanoparticles.

BACKGROUND OF THE INVENTION

It is known that antibodies bind with antigens as part of the human disease defense system. Presently, antigens are detected by such techniques as immunofluorescence, immunoperoxidase, or enzyme-linked immunosorbent assay (ELISA), each of which then employs a microscope for visual detection of the target antigen. It is desirable to exploit the use of magnetic signaling technology to automate the detection of analytes, such as antigens, and to further apply this technology to the detection of any biological matter. Still further, it is important to ensure that the equipment utilized is reliable and accurate in the detection of analytes.

SUMMARY OF THE INVENTION

Electromagnetic read heads are useful in detecting analytes via nanoparticle-labeled substances. However, is important to ensure that the equipment utilized to detect the antigens is reliable and accurate. Accordingly, one embodiment of the invention includes a calibration assembly which has nanoparticles with known magnetic properties, the nanoparticles spaced apart at known y-axis locations along the calibration assembly.

For example, an embodiment of forming a calibration assembly includes forming at least one calibration trench within an outer layer. The calibration trench extends along a y-axis. An encapsulation layer is formed within the calibration trench and a plurality of nanoparticles spaced apart along the y-axis are provided in the encapsulation layer. Each of the plurality of nanoparticles are provided at known y-axis locations in the calibration trench. Further, each of the plurality of nanoparticles have a known magnetic property. The encapsulation is cured such that the plurality of nanoparticles are encapsulated within the encapsulation layer at the known y-axis locations.

The calibration assembly may be used to calibrate a matched filter of the write and read circuitry. Because the calibration assembly comprises nanoparticles with known magnetic properties the read response of the read circuitry to a particular nanoparticle may be stored in the matched filter as an ideal signal for that nanoparticle. The ideal signal stored in the matched filter may then be utilized for reliably and accurately detecting antigens. Still further, the ideal signal stored within the matched filter of the write and read circuitry may be utilized in a manufacturer's or user's correlation test of a calibration assembly to ensure that the calibration assembly is within the manufacturer's or user's acceptable standards for calibration of their write and read assemblies.

For a fuller understanding of the present invention, reference should be made to the following detailed description taken in conjunction with the accompanying drawings.

BRIEF DESCRIPTION OF THE DRAWINGS

FIG. 1 is a top view of a calibration assembly, not to scale, in accordance with an embodiment of the invention;

FIG. 2C is a cross-sectional view of calibration assembly, not to scale, including calibration trenches and an alignment trench in accordance with an embodiment of the invention;

DETAILED DESCRIPTION OF THE INVENTION

Figure 2A:
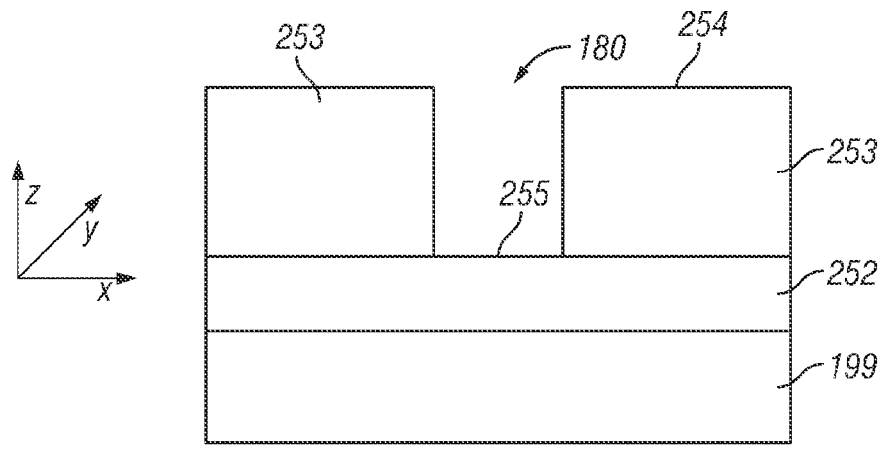
FIG. 2A is a cross-sectional view of a portion of a calibration assembly, not to scale, including a calibration trench in accordance with an embodiment of the invention.

The present invention is described in exemplary embodiments in the following description with reference to the Figures, in which like numbers represent the same or similar elements. While the invention is described in terms of the best mode for achieving the invention's objectives, it will be appreciated by those skilled in the art that variations may be accomplished in view of these teachings without deviating from the spirit or scope of the invention.

In copending and coassigned U.S. patent application Ser. No. 12/888,388 entitled "DETECTION OF ANALYTES VIA NANOPARTICLE-LABELED SUBSTANCES WITH ELECTROMAGNETIC READ-WRITE HEADS", and Ser. No. 12/970,837 entitled "TRENCHED SAMPLE ASSEMBLY FOR DETECTION OF ANALYTES WITH ELECTROMAGNETIC READ-WRITE HEADS," a sample assembly and method of detecting antigens is described utilizing electromagnetic read heads and are hereby incorporated by reference.

It is important to ensure that the equipment utilized to detect antigens is reliable and accurate. Accordingly, one embodiment of the invention includes a calibration assembly having nanoparticles, with known magnetic properties, spaced apart at known y-axis locations along the calibration assembly. In one embodiment, the calibration assembly may be used to calibrate a matched filter of the write and read circuitry. Because the calibration assembly comprises nanoparticles with known magnetic properties the read response of the read circuitry to a particular nanoparticle may be stored in the matched filter as an ideal signal for that nanoparticle. The ideal signal stored in the matched filter may then be utilized for reliably and accurately detecting antigens. Still further, the ideal signal stored within the matched filter of the write and read circuitry may be utilized in a manufacturer's or user's correlation test of a calibration assembly to ensure that the calibration assembly is within the manufacturer's or user's acceptable standards for calibration of their write and read assemblies.

Magnetic sensors, such as GMR sensors, contain magnetic materials whose combined effect is to have a resistance change when subjected to a magnetic field. When subjected to low-level electrical overstress (EOS) or electrostatic discharge (ESD) current/voltage pulses the GMR sensors can be damaged or degraded. Still further, corrosion can damage magnetic sensors over time, reducing the signal strength and possibly leading to failure. In one embodiment, a method of determining if a read sensor is damaged or degraded is described. Still further, if it is determined that a read sensor is degraded, a method of calibrating a read sensor is described. Calibration of each individual read sensor allows for uniform read responses from each of the read sensors on a read head, and prevents unreliable an inaccurate detection of analytes due to sensor degradation.

FIG. 1 is a top view of a calibration assembly 100, not to scale, in accordance an embodiment of the invention. The calibration assembly 100 includes a substrate 199. The substrate 199 may comprise, without limitations, a Peltier hard-substrate, a glass substrate, a polyethylene terephthalate (PET, which is commonly known by the trade name of Mylar™) substrate, a flexible-substrate, or other materials having similar properties. The term "substrate" refers to any supporting structure, including, but not limited to, the substrates described above. Further, the substrate may include of more than one layer of material.

Figure 2B:
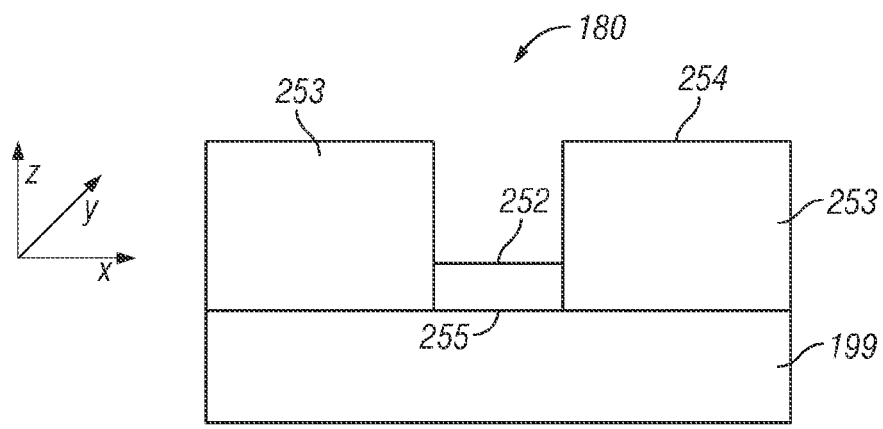
FIG. 2B is a cross-sectional view of a portion of a calibration assembly, not to scale, including a calibration trench in accordance with an embodiment of the invention.

As shown in FIGS. 2A, 2B, and 2C, an outer layer 253 is formed over substrate 199. Deposition techniques utilized herein include, but are not limited to, photolithography, silk-screening, and other similar processes. The outer layer may comprise diamond-like-carbon, polytetrafluoroethylene, aluminum oxide, polyamides, or other low-friction materials known in the art. The outer layer 253 may be formed to a thickness of between 0.2 to 60 microns. The outer layer 253 includes calibration trenches 180. The process of forming the calibration trenches 180 is described with respect to FIGS. 2A and 2B.

One embodiment of forming calibration trenches 180 is illustrated in FIG. 2A. In this embodiment, a base layer 252 is formed on substrate 199. Base layer 252 may comprise nonmagnetic materials such as gold, silicon, or $SiO_2$, or other materials having similar magnetic properties, without limitation. An outer layer 253 is then formed on base layer 252. Outer layer 253 has an upper surface 254. A plurality of calibration trenches 180 are formed within outer layer 253. Calibration trenches 180 may be formed by known methods in the art including laser milling, x-ray milling, or photolithographically. Calibration trenches 180 may be formed to have a depth of between 0.2 to 60 microns. It should be understood by one of ordinary skill in the art that, while only one calibration trench is shown, a plurality of calibration trenches 180 may be formed within the outer layer 253 with the same method described herein. Each calibration trench 180 is formed having a bottom surface 255. In one embodiment, the bottom surface of the trench exposes base layer 252.

Another embodiment of forming calibration trenches 180 is described with respect to FIG. 2B. In this embodiment, outer layer 253 is formed on substrate 199. The outer layer 253 has an upper surface 254. A plurality of calibration trenches 180 are formed within outer layer 253. Calibration trenches 180 may be formed by known methods in the art including laser milling, x-ray milling, or photolithographically. Calibration trenches may be formed to have a depth of between 0.2 to 60 microns. It should be understood by one of ordinary skill in the art that, while only one calibration trench is shown, a plurality of calibration trenches 180 may be formed within the outer layer 253 with the same methods described herein. Each calibration trench 180 is formed having a bottom surface 255. Base layer 252 is formed within each calibration trench 180 and on the bottom surface 255 of each calibration trench 180. Base layer 252 may comprise nonmagnetic materials such as gold, silicon, or $SiO_2$, or other materials having similar magnetic properties, without limitations. As shown in FIG. 2B, the base layer 252 only partially fills calibration trenches 180. There are many embodiments in which base layer 252 may be formed to only partially fill calibration trenches 180. For example, in one embodiment, base layer 252 may be formed conformally over the outer layer 253 and within calibration trenches 180. Base layer may then be removed by etching or planarization techniques known in the art. Alternatively, the base layer 252 may be selectively deposited by known methods in the art. The described embodiment of forming a base layer 252 only within the calibration trench 180 is particularly advantageous in embodiments in which expensive materials are utilized, such as gold since much less material is required to form the base layer 252.

It is important to note that the base layer 252 may be omitted when forming the calibration assembly 100. However, the base layer may be formed on the substrate 199 in order for the calibration assembly 100 to be similar to that of a sample assembly as described in copending and coassigned U.S. patent application Ser. No. 12/970,837 entitled "TRENCHED SAMPLE ASSEMBLY FOR DETECTION OF ANALYTES WITH ELECTROMAGNETIC READ-WRITE HEADS."

For example, as shown in FIG. 1, eight calibration trenches 180 may be formed to correspond to the head-module 104 of the IBM® TS 1130 writing with eight write elements 106 and reading with eight read sensors 108 simultaneously, as further explained below. The calibration trenches 180 are parallel to each other and extend in along the y-axis.

In one embodiment, as shown in FIGS. 1 and 2C, the outer layer 253 further includes at least one servo alignment track 194 with a plurality of magnetic servo alignment marks 193. The servo alignment track 194 is parallel with the calibration trenches 180 and extends along the y-axis. The servo alignment track 194 may be a servo alignment trench 194 with a plurality of magnetic servo alignment marks 193. FIG. 2C shows a cross section of substrate 199 along the x-axis illustrating an embodiment in which an alignment trench 194 is formed within outer layer 253. For simplicity of illustration, base layer 252 is not illustrated in FIG. 2C. Alignment trench 194 may be formed in the same manner as described for forming calibration trenches 180 shown in FIGS. 2A and 2B. In one embodiment, alignment trench 194 is formed simultaneously with the formation of calibration trenches 180. Specifically, alignment trench 194 may be formed by known methods in the art including laser milling, x-ray milling, or photolithographically. Alignment trench 194 may have a depth of between 0.2 to 60 microns. It should be understood by one of ordinary skill in the art that, while only one alignment trench 194 is shown, a plurality of alignment trenches 194 may be formed within the outer layer 253 as described herein. For example, alignment trenches 194 could be formed between each of the calibration trenches 180.

In this embodiment, calibration trenches 180 may be masked and the servo alignment trench 194 is filled with tape ink. The tape ink, which contains magnetic recording particles in a polymer matrix, is cured by methods known in the art. Magnetic encoded servo alignment marks 193 are subsequently encoded in the cured tape ink.

In another embodiment, magnetic encoded servo alignment marks 193 are encoded on a piece of magnetic tape which is adhered to outer layer 253. Further, the magnetic encoded servo alignment marks 193 may be encoded by the manufacturer of substrate 199 on the magnetic tape. Magnetic encoded servo alignment marks 193 may be in the form of timing based servo marks as taught by U.S. Pat. No. 7,639,448 entitled "Differential Timing Based Servo Pattern for Magnetic-Based Storage Media," which is hereby incorporated by reference in its entirety. Servo alignment marks 193 are read by read sensor 108 and used to keep the write elements 106 and read sensors 108 in alignment with calibration trenches 180 along the x-axis while the head module 104 moves relative to calibration trenches 180 along the y-axis.

Still further, in one embodiment the alignment marks 193 may be non-magnetic marks. For example, the alignment marks may be lithographed, silk-screened or ink-jet printed, and read with an optical laser.

Figure 3A:
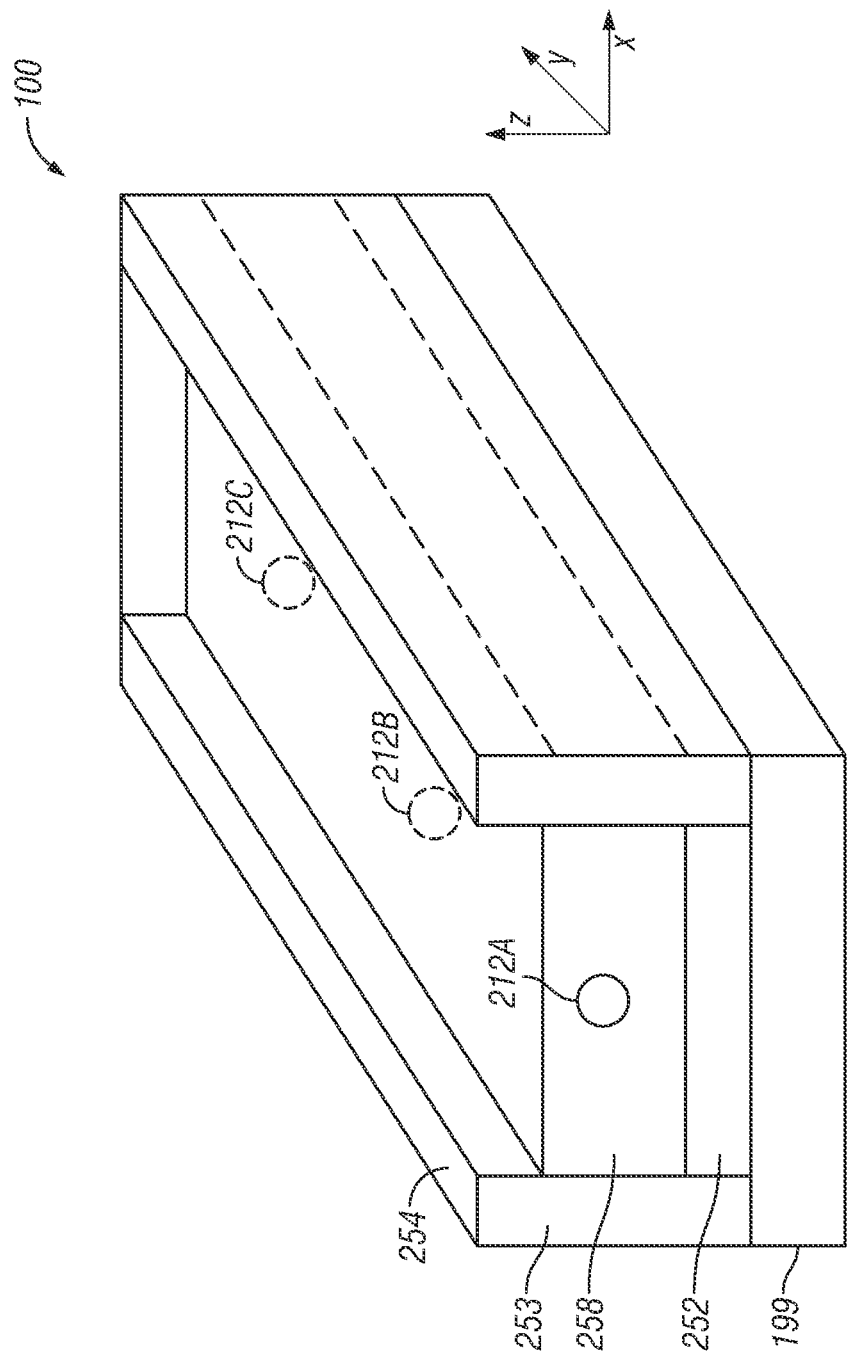
FIG. 3A illustrates a plan view of the calibration assembly, not to scale, having nanoparticles placed at known y-axis locations in accordance with an embodiment of the invention.
Figure 3B:
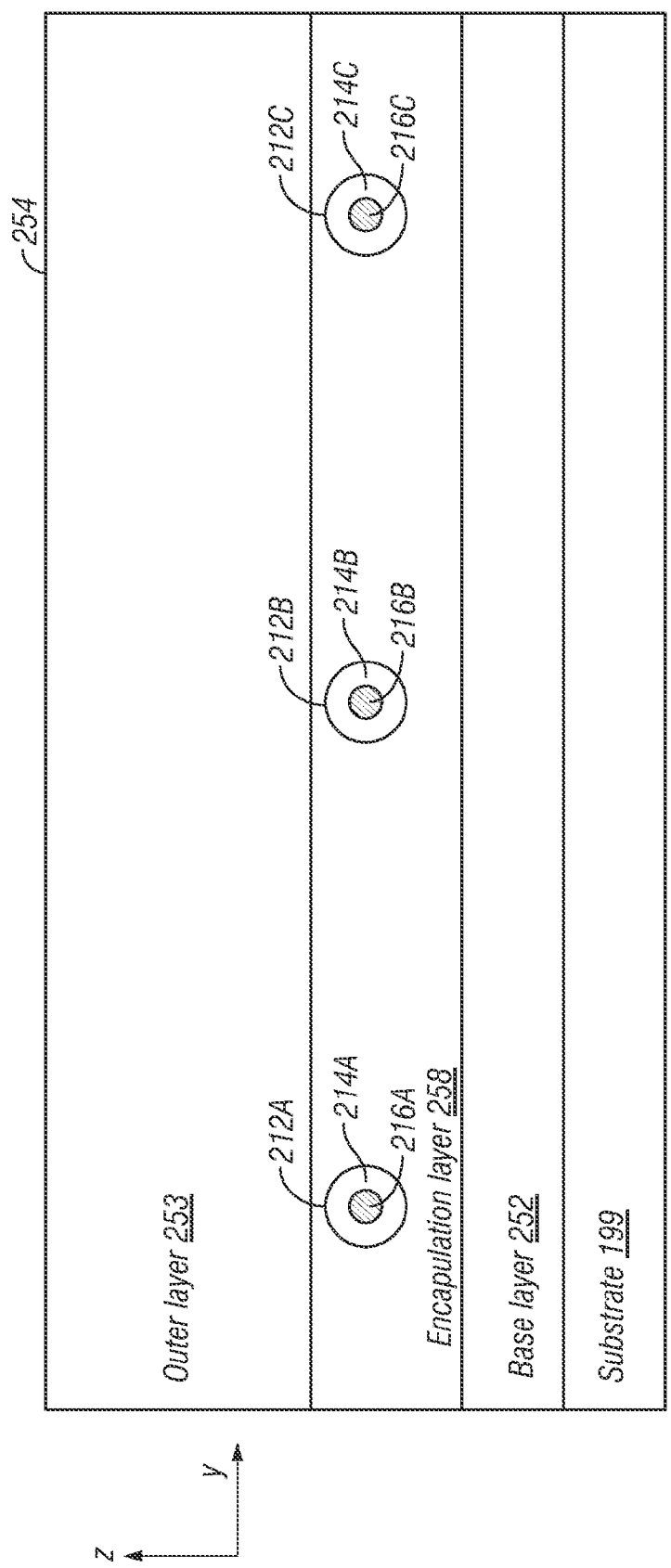
FIG. 3B is a cross-sectional view of the calibration assembly, not to scale, having nanoparticles in accordance with an embodiment of the invention.
Figure 3C:
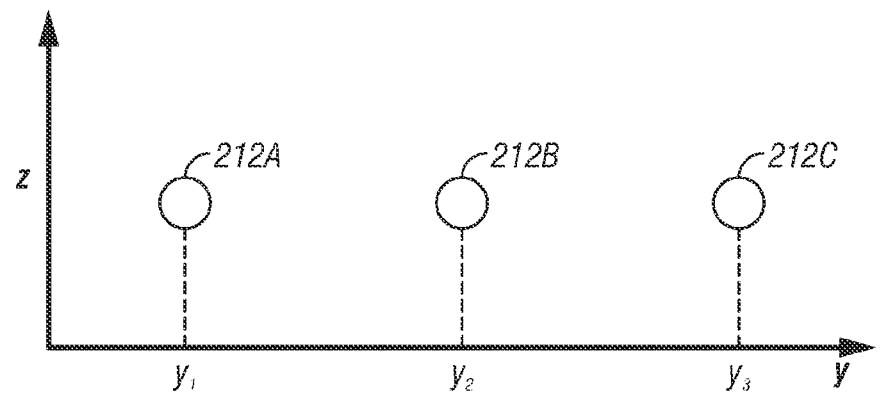
FIG. 3C is a graphical representation of the calibration assembly, not to scale, having nanoparticles at known y-axis locations in accordance with an embodiment of the invention.
Figure 4:
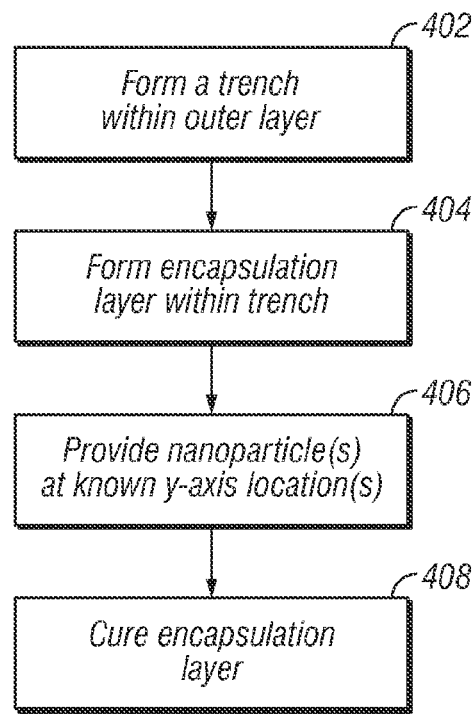
FIG. 4 is a flow chart illustrating the steps of preparing the calibration assembly in accordance with an embodiment of the invention.

The preparation of the calibration assembly 100, including the formation of the nanoparticles within the calibration trench 180 is discussed further with respect to FIGS. 3A, 3B, 3C and 4. FIG. 3A illustrates plan view of calibration assembly 100 having nanoparticles 212A, 212B, and 212C placed at known y-axis locations. FIG. 3B is a cross-sectional view of the calibration assembly 100 having nanoparticles 212A, 212B and 212C. FIG. 3C is a graphical representation of the calibration assembly 100 having nanoparticles at known y-axis locations. FIG. 4 illustrates the steps of preparing the calibration assembly 100. For simplicity of explanation, FIGS. 3A, 3B and 3C show only a single calibration trench 180 and an embodiment in which the base layer 252 is formed within the calibration trench 180. However, it should be understood that the calibration assembly 100 may have a plurality of calibration trenches 180 and the base layer may be formed by any of the methods described herein. Similarly, although FIGS. 3A, 3B, and 3C show only three nanoparticles 212, one of ordinary skill in the art would understand that any number of nanoparticles 212 may be provided.

As discussed above, an outer layer 253 is formed on substrate 199. In step 402, at least one calibration trench 180 is formed in outer layer 253. Base layer 252 is formed on the bottom surface 255 of the calibration trench 180.

In step 404, an encapsulation layer 258 is formed within the calibration trench 180. The encapsulation layer 258 may comprise a polymer resin including epoxies, acrylates, cyanoacrylates and silicones. The encapsulation layer 258 may include the addition of a thermal polymerization initiator such as azobisiobutyronitrile, or a UV polymerization initiator such as benzoylperoxide.

In step 406, nanoparticles 212A, 212B and 212C are provided at known spaced apart y-axis locations within the calibration trench 180. For example, as shown in FIG. 3C, nanoparticle 212A is located at the y-axis location of calibration trench 180 at $y_1$. Further, nanoparticle 212B is located at the y-axis location of calibration trench 180 at $y_2$. Still further, nanoparticle 212C is located at the y-axis location of calibration trench 180 at $y_3$. As shown in FIG. 3B, the nanoparticles 212A, 212B and 212C (which may hereinafter be referred to as 212) include a magnetic inner core 216A, 216B, and 216C (which may hereinafter be referred to as 216) and an outer shell 214A, 214B, and 214C (which may hereinafter be referred to as 214). Magnetic inner cores 216 may comprise hard magnetic materials with high coercivity, such as $Fe_2O_3$, $CrO_2$, and Barium Ferrite BaFe. For example, magnetic inner cores 216 may comprise iron oxide based nanoparticle materials, including M $Fe_2O_4$ (where M may be Co, Ni, Cu, Zn, Cr, Ti, Ba, or Mg) nanomaterials, and iron oxide coated nanoparticle materials or other structures with similar functionality. The inner cores 216 are coated with an outer-shell 214 of nonmagnetic gold, silicon, or $SiO_2$, to create nanoparticles 212.

In one embodiment, the nanoparticles 212A, 212B, and 212C are the same nanoparticle (e.g. the same inner core 216 with the same outer shell 214) such that the nanoparticles 212A, 212B, and 212C have the same magnetic properties. In other embodiments, at least one of nanoparticles 212A, 212B, and 212C may be different than the other nanoparticles 212A. 212B, and 212C (e.g. may have at least one of a different inner core 216 and a different outer shell 214) such that the at least one nanoparticle 212A, 212B, and 212C has different magnetic properties than the other nanoparticles 212A, 212B, and 212C. In either embodiment, the magnetic properties of each nanoparticle 212A, 212B, and 212C at each y-axis location is known.

It is important to note that magnetized nanoparticles are prone to agglomerate and form lumps. Therefore, in one embodiment, the magnetic inner cores 216 of nanoparticles 212 are demagnetized. For example, in one embodiment, the magnetic inner cores 216 of nanoparticles 212 are heated above their Curie temperature to demagnetize the inner cores 216. The heated magnetic inner cores 216 are allowed to cool. The aforementioned demagnetization step keeps the inner cores 216 of nanoparticles 212 as individual particles.

In another embodiment, the step of demagnetizing the inner cores 216 of nanoparticles may be omitted. The process of manufacturing the inner cores 216 of nanoparticles may include a step of high temperature sintering. Thus, the manufacturing process of the nanoparticles 212 may demagnetize the inner cores 216. The formation of nanoparticles is taught without limitation by U.S. Pat. No. 6,962,685, entitled "Synthesis of Magnetite Nanoparticles and the Process of Forming," which is hereby incorporated by reference in its entirety.

In step 408 the encapsulation layer 258 is cured. As described above, the encapsulation layer 258 may include the addition of a thermal polymerization initiator such as azobisiobutyronitrile, or a UV polymerization initiator such as benzoylperoxide. Accordingly, a thermal curing treatment or UV exposure curing treatment may be performed on calibration assembly 100 such that the encapsulation layer 258 hardens and encapsulates the nanoparticles 212A, 212B, and 212C at their respective known $y_1$, $y_2$, and $y_3$ locations Returning to FIG. 1, head module 104 includes electromagnetic write-heads 106 and magneto-resistive read sensors 108 arranged in pairs, such that each write head 106 is paired with a read sensor 108. The write head 106 may be a thin film write element. The electromagnetic write-heads 106 first write to calibration trenches 180, and then the adjacent magneto-resistive read sensors 108 immediately reads from calibration trenches 180, which is referred to as a read-after-write operation. In an exemplary embodiment of the invention, the calibration assembly 100 has eight calibration trenches 180 corresponding to eight bits in a byte. Accordingly, in this embodiment, the head module includes eight electromagnetic write-head 106 and magnetoresistive read sensor 108 pairs. Advantageously, this is the same number of write heads and read sensors in a typical head-module used in magnetic tape drive products, such as IBM® TS 1130. Therefore, in one embodiment the head module 104 may be an IBM® TS 1130 head module. It should be understood, however, any number of calibration trenches 180 may be used, and the number of electromagnetic write-head 106 and magneto-resistive read sensor 108 pairs in head-module 104 may be any number. The number may be in the range from one to the number of electromagnetic write-head and magneto-resistive read sensor pairs the head-module 104. For example, in an embodiment in which there are sixteen such electromagnetic write-head and magneto-resistive read sensor pairs, such as in a head module of an IBM® 3480 tape drive, the number of calibration trenches may be sixteen. In one embodiment, the number of calibration trenches 180 is an integral multiple of the number of write-head 106 and read sensor 108 pairs. Still further, in one embodiment, the write-head 106 and the read sensor are not separate devices. Instead a single head may perform the functions of both the write-head 106 and read sensor 108.

As mentioned above, the calibration trenches 180 may have spacing from one calibration trench to the adjacent calibration trench along the x-axis to match the spacing from one read sensor 108 to the adjacent read sensor 108 along the x-axis. In one embodiment the spacing between one calibration trench 180 and an adjacent calibration trench 180 is 166.5 microns to match the read sensor to read sensor spacing of the TS1130 tape drive.

Write-heads 106 may be any write head known in the art. In one embodiment write-heads 106 comprise miniature electromagnets, with a coil sandwiched between two poles. Read sensors 108 may be anisotropic magneto-resistive (AMR), giant magneto-resistive (GMR), or tunnel magneto-resistive (TMR) read sensors, or other devices with similar functionality known in the art. AMR sensors are made from magnetic alloys with intrinsic magnetoresistive (MR) behaviors. GMR read sensors, which are also known as spin-valve read sensors have synthetic MR properties composed of multi-layered magnetic and non-magnetic materials. A GMR sensor typically has a conductive metal (often Cu) sandwiched between a ferromagnetic pinned layer (PL2) and a soft magnetic free layer (FL). The GMR effect arises from electrons scattering off the PL2 and FL such that the scattering depends on the cosine of the angle between the magnetic moments in PL2 and FL. Typically, a GMR has an additional ferromagnetic pinned layer (PL1) which is magnetized anti-parallel, to PL1. There are several reasons for using anti-parallel PL1 and PL2 rather than a single PL2.

To achieve a high GMR effect requires a thicker PL2. In order to tune the GMR sensor, though, it is desired to have a low net moment impinging on the FL. To do so, would require a thin PL2, which is both difficult to control in a process, is less stable, and has a lower GMR ratio than a thick PL2. The above mentioned criteria can be satisfied by making PL2 and PL1 anti-ferromagnetically coupled ferromagnets. Furthermore, since PL1 and PL2 have a very strong antiferromagnetic coupling, they are highly stable. TMR read sensors may utilize a tunnel barrier layer to augment the GMR internal structure and to provide increased sensitivity.

As shown in FIG. 1, write-head 106 may be longer along the x-axis direction than read sensor 108. Accordingly, the active sensing portion of read sensor 108 is smaller than write-head 106, along the x-axis. Write-head 106 is used to magnetize nanoparticles 212A, 212B, and 212C for detection by read sensor 108 as discussed below. It is advantageous for write-head to be longer in the x-direction than read sensor 108 because it prevents read sensor from encountering unmagnetized nanoparticles, and thus, registering a false-negative detection of a nanoparticle 212A, 212B, 212C.

Head-module 104 is kept in linear alignment with calibration trenches 180 along the x-axis by position-error-servo (PES) read-head 192, which reads magnetically encoded servo-alignment marks 193 from servo track 194 on calibration assembly 100. PES read-head 192 may be, for example, an AMR, GMR, or TMR read sensor. In the example illustrated in FIG. 1, servo-alignment marks 193 shown are Timing Based Servo (TBS) servo-alignment marks such as those used in IBM® Linear Tape Open (LTO) tape drive products (e.g., IBM® tape product models TS1120 and TS1130). U.S. Pat. No. 6,320,719, entitled "Timing Based Servo System for Magnetic Tape Systems," is hereby incorporated by reference in its entirety for its showing of Timing Based Servo control and TBS servo-alignment marks. U.S. Pat. No. 6,282,051, entitled "Timing Based Servo System for Magnetic Tape Systems," is hereby incorporated by reference in its entirety for showing the writing of TBS servo-alignment marks.

Figure 5:
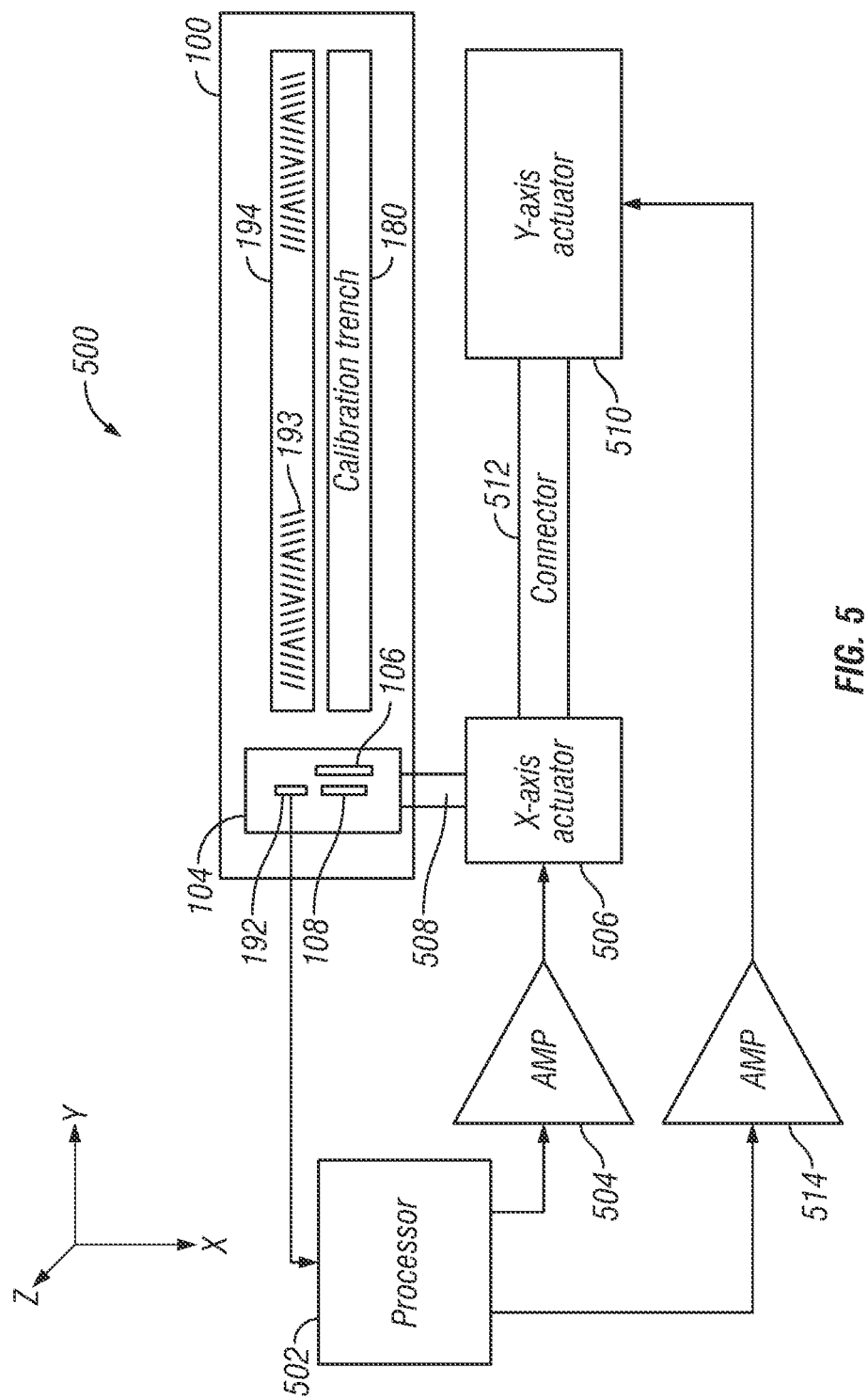
FIG. 5 illustrates control circuitry for the x-axis and y-axis motion of the head-module in an embodiment of the invention.

FIG. 5 illustrates an embodiment of a servo control system 500 for controlling the motion of head-module 104 in the x-axis and y-axis. For simplicity, FIG. 5 illustrates calibration assembly 100 including a single trench 180. In addition, FIG. 5 shows a head module including a single write-head 106 and read sensor 108 pair and a PES read head 192. However, it should be understood that the calibration assembly 100 may include a plurality of trenches and the head module 104 may include a plurality of write-heads 106 and read sensors 108. PES read-head 192 reads servo-alignment marks 193 in servo track 194. Processor 502 receives position-error-servo (PES) signals from PES read-head 192. Processor 502 sends a signal to power amplifier 504 to control x-axis actuator 506 based on the PES information. In turn, the x-axis actuator 506 controls the motion of head module 104 in the x-axis direction. X-axis actuator 506 is connected to head-module 104 via mechanical connector 508. Accordingly, head-module 104 can be positioned to center write-head 106 and read sensor 108 on calibration trenches 180 of calibration assembly 100. Processor 502 also sends signals to power amplifier 514 to control y-axis actuator 510 for conducting a scan by head module 104 across calibration assembly 100. Y-axis actuator 510 is connected to x-axis actuator via mechanical connector 512, such that head-module 104 can be moved along the y-axis in a controllable manner.

Figure 6:
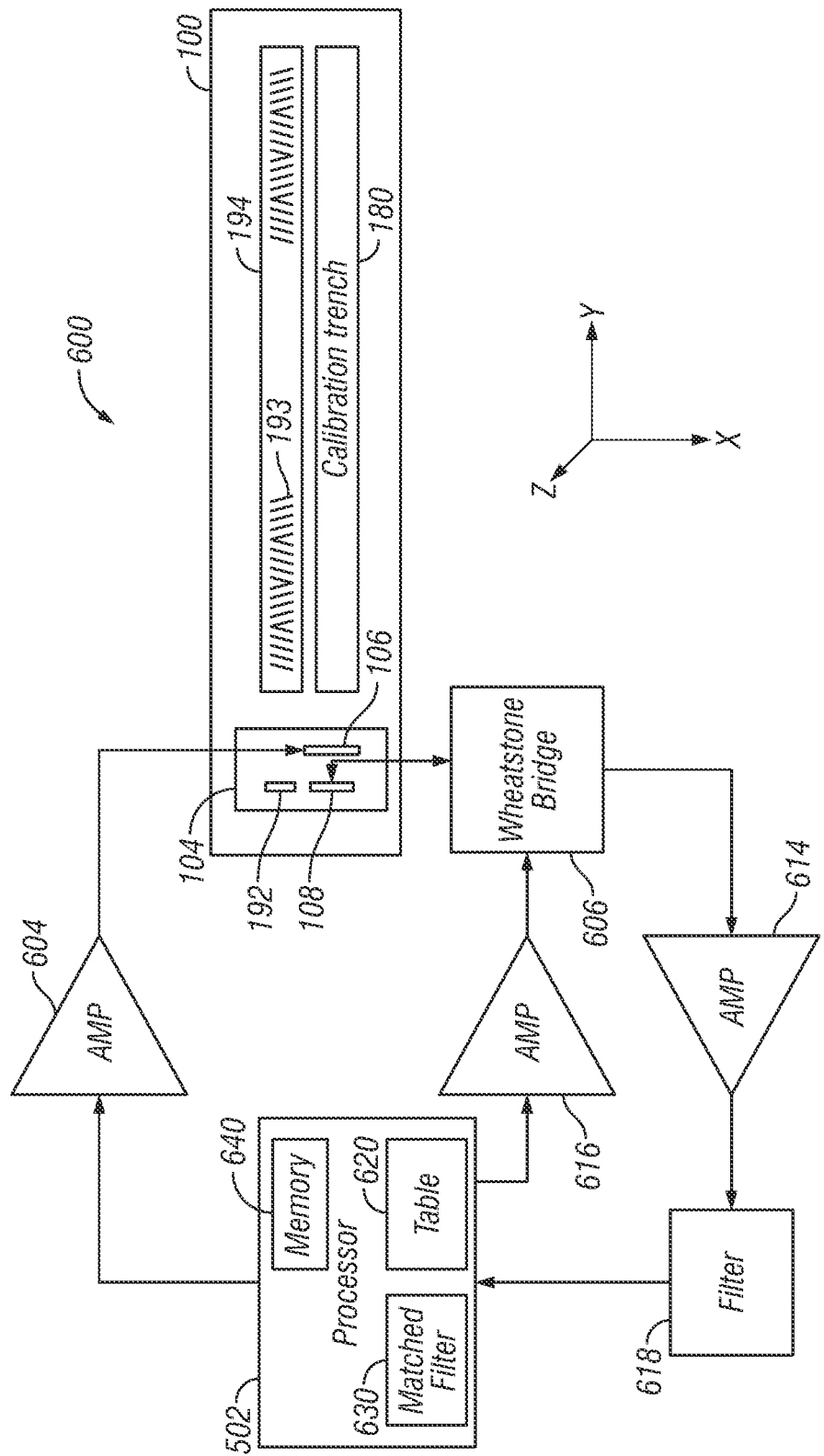
FIG. 6 illustrates read and write circuitry in an embodiment of the invention.

FIG. 6 illustrates one embodiment of a write and read circuitry 600 for use in writing to the calibration trenches 180 (i.e., magnetizing nanoparticles 212) and reading from the calibration trenches 180 (i.e., sensing and detecting the magnetized nanoparticles 212). For simplicity, FIG. 6 illustrates calibration assembly 100 including a single trench 180. In addition, FIG. 6 shows a head module including a single write-head 106 and read sensor 108 pair. However, it should be understood that the calibration assembly 100 may include a plurality of trenches and the head module 104 may include a plurality of write-heads 106 and read sensors 108.

Processor 502 sends signals to power amplifier 604. Power amplifier provides power to write-head 106 for magnetizing nanoparticles 212. Processor 502 also sends signals to power amplifier 616. Power amplifier 616 powers Wheatstone bridge 606. In one embodiment, Wheatstone bridge 606 includes read sensor 108 as one leg of the Wheatstone bridge and the remaining three legs of the Wheatstone bridge are resistors of the same nominal resistance as read sensor 108. One of these resistors in Wheatstone bridge 606 may be adjustable so that the Wheatstone bridge may be balanced to a null output when read sensor 108 is not experiencing a magnetic field from a magnetized inner core 216 of nanoparticles 212. Thus, read sensor 108 receives DC current from the Wheatstone bridge 606. Read sensor 108 detects a resistance change based on the magnetic field provided by the magnetized inner cores 216 of nanoparticles 212. Wheatstone bridge 606 balances out the zero-magnetism resistance of read sensor 108 such that only the change in resistance of read sensor 108 is sent to amplifier 614. The amplifier 614 receives the change in resistance and sends the change in resistance to processor 502 through filter 618. Filter 618 filters out noise. In one embodiment, filter 618 filters out 60 Hz noise, and any harmonics thereof, which is the type of noise that is pervasive in an office or laboratory setting in which processes of the invention may be performed.

Processor 502 includes a matched filter 630, a table 620, and memory 640. Processor 502 determines if a nanoparticle 212 was detected, and which nanoparticle 212 was detected utilizing the matched filter 630 and table 620. The change in resistance of read sensor 108 is directly proportional to the magnetic field provided by nanoparticle 212. The identification of the various nanoparticles simultaneously in the same sample assembly may be facilitated by the table 620 in processor 502. For example, a lookup table 620 contains a list of (a) nanoparticles and (b) the coercivity of the inner cores 216 of nanoparticles.

In one embodiment, the calibration assembly 100 may be used to calibrate the matched filter 630 of the write and read circuitry 600. Because the calibration assembly 100 comprises nanoparticles 212 with known magnetic properties the read response of the read circuitry to a particular nanoparticle may be stored in the matched filter 630 as an ideal signal for that nanoparticle. The ideal signal stored in the matched filter may then be utilized for reliably and accurately detecting antigens.

For example, a correlation calculation is performed by the write and read circuit 600 of FIG. 6 to improve the detection accuracy of the nanoparticles 212. The processor 502 performs correlation calculation C(y) shown in Equation 1 between a detection signal profile g(y) read by read sensor 108 when a nanoparticle 212 is detected and a matched filter 630.

$$C(y)=\int g(\eta)h(\eta-y)d\eta \qquad \text{Equation 1}$$

In Equation 1, η is the integration variable along the y-axis that varies as read sensor 108 sweeps along the y-axis. The matched filter 630 includes an impulse response h(y) of an ideal signal profile of a detected nanoparticle 212. Since h(y) is used repetitively, it may be calculated once and stored as matched filter 630 in processor 502. For example FIG. 7 illustrates the process of calculating an impulse response h(y) of an ideal signal profile of a detected nanoparticle.

Figure 7:
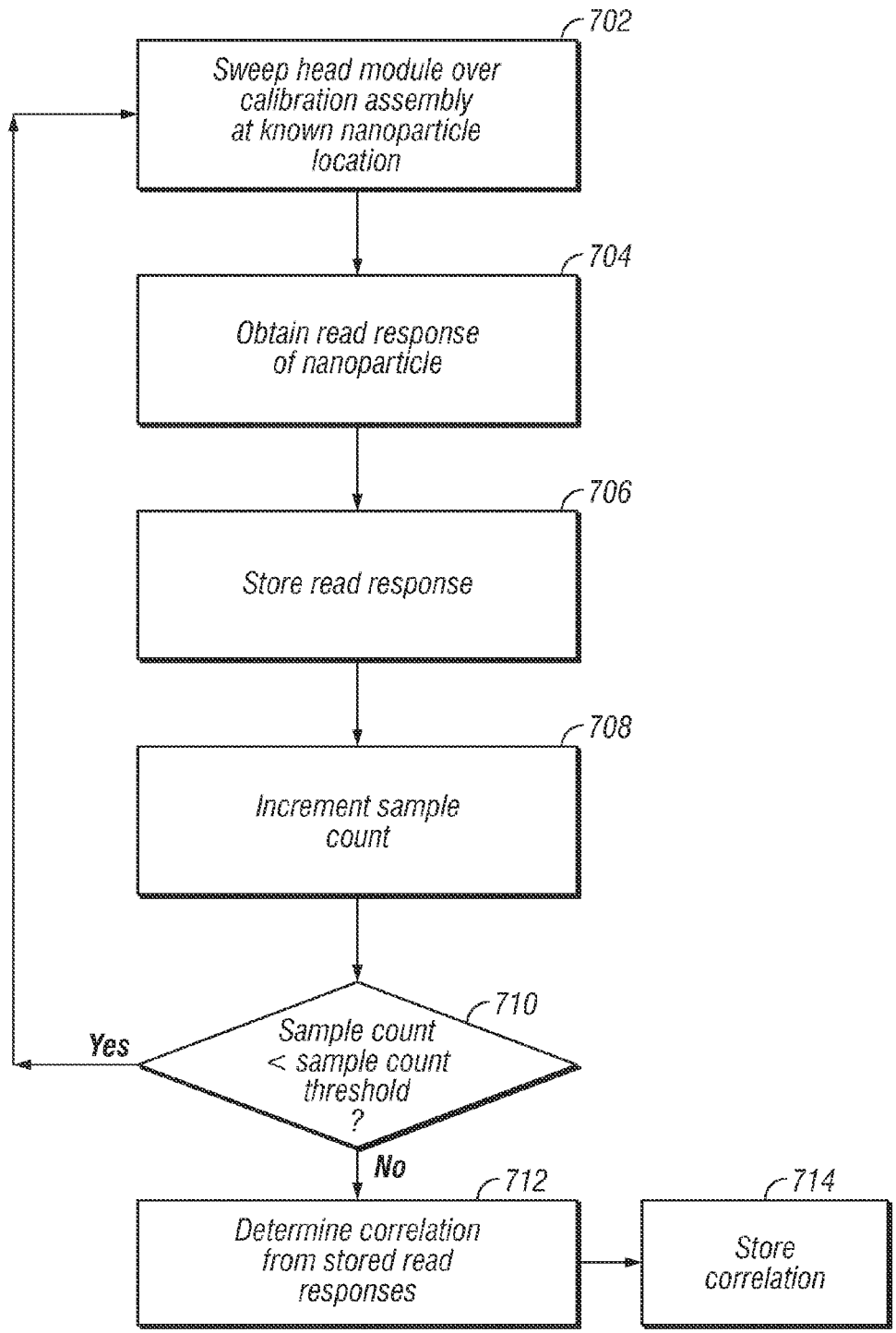
FIG. 7 is a flow chart illustrating the process of calculating an impulse response of an ideal signal profile of a detected nanoparticle in accordance with an embodiment of the invention.

Turning to FIG. 7, in step 702, the head module 104 with at least one magneto-resistive read sensor 108 is swept along the y-axis of the calibration assembly 100 at a known nanoparticle 212 location. For example, the head module 104 is swept along the y-axis of the calibration assembly 100 at location $y_1$ shown in FIG. 3C where it is known nanoparticle 212A is located. The magnetic properties of nanoparticle 212A are known.

In one embodiment head-module 104 is moved linearly from left to right along the +y axis relative to a stationary calibration assembly. In another embodiment, the calibration assembly 100 is swept linearly from right to left along the -y axis past a stationary head-module 104. If substrate 199 is of a flexible polyethylene terephthalate material, then in one embodiment, this right-to-left motion may be performed as data read-write operations in a magnetic tape drive. The head module 104 may sample a single calibration trench 180, or simultaneously sample a plurality of calibration trenches 180. As an alternate embodiment, head-module 104 comprises a helical-scan rotary head-module, and the y-axis of the calibration trench 180 is at an angle to the substrate 199. In this embodiment, the calibration trenches 180 are much shorter in length such that alignment of the head module 104 with calibration trenches 180 may be accomplished without alignment marks 193. In one embodiment the IBM® MSS 3850 helical-scan tape drive may be utilized to detect nanoparticles 212.

In one embodiment the head module 104 comes into physical contact with the upper surface 254 of the outer layer 253 during the sweeping step of 702. Keeping the head module 104 in physical contact with the upper surface ensures that the head module 104 is kept at a known z-axis position and assists with alignment of head module 104 with calibration trenches 180. As discussed above, the outer layer 253 may comprise diamond-like-carbon, polytetrafluoroethylene, aluminum oxide, polyamides, or other low-friction materials known in the art. Accordingly, the low friction material of the outer layer assists the head module 104 to smoothly sweep the calibration trenches 180 while in physical contact with the upper surface 254 of outer layer 253, such that the nanoparticles of the calibration trench 180 are reliably and accurately detected.

As discussed with respect to step 406 in FIG. 4, in some embodiments the inner core 216 of nanoparticles are demagnetized. Accordingly, in this embodiment, as part of step 702, write-head 106 writes to nanoparticles 212A, 212B, and 212C to magnetize inner cores 216A, 212B, and 212C of nanoparticles. Write-head 106 writes with a constant DC magnetic polarity for the duration of the sweeping step 702, such that there are no unwritten regions of calibration assembly 100. In one embodiment, write-head 106 writes with magnetically-overlapping write pulses. Further in step 702, read sensor 108 detects the freshly magnetized inner cores 216A, 216B, and 216C of nanoparticles 212A, 212B, and 212C.

Write head 106 magnetizes the inner cores 216 of nanoparticles 212 along the y-axis, which is the longitudinal-recording in the tape drive industry. Read sensor 108 magnetically detects nanoparticles 212 along the y-axis. As a result, in step 702, the nanoparticles 212 may be magnetized by write-head 106 and then immediately and magnetically detected by read sensor 108 during a single sweep of the calibration trenches 180. As discussed above, this process is referred to as a read-after-write operation. In one embodiment the write-head 106 and read sensor 108 are separated by a magnetic shield (not shown) to prevent cross-talk between write-head 106 and read sensor 108 during step 702.

In another embodiment, the write-head 106 and the read sensor 108 are physically separated sufficiently to avoid pick-up by the read sensors 108 of the magnetic signals emanating from the write head 106 during the read-after-write operation. This embodiment can be accomplished by locating the write-heads 106 in separate module(s) from the read sensors 108 and aligning the read sensor 108 and write-head 106 pair(s) with a precision alignment tool and bonding the modules together.

Alternatively, the steps of magnetizing nanoparticles 212 and the step of detecting the nanoparticles 212 may be performed separately. For example, write head 106 magnetizes inner cores 216 of nanoparticles 212 along the y-axis of calibration assembly 100. In one embodiment, write-head 106 is then turned off. Subsequently, read sensor 108 magnetically detects nanoparticles 212 along the y-axis. The read module sensor 108 may be swept across calibration trenches 180 along the y-axis in both the +y and −y directions. Accordingly, read sensor 108 can repeatedly check for magnetized nanoparticles 212.

In an embodiment in which the number of calibration trenches 180 are greater than the number of write-head 106 and read sensor 108 pairs in head-module 104, the head-module 104 may scan the calibration trenches 180 in a serpentine fashion. The head-module 104 performs a scan in the +y direction, as head-module 104 only provides read-after-write capability in the +y direction as shown in FIG. 1. Then, a second head-module (not shown) comprising a mirror image of head-module 104, conducts a read-after-write operation in the −y direction.

In step 704, a read response is obtained for the nanoparticle 212. Read sensor 108 detects the magnetic properties of an inner core 216 based on the materials used for that inner core 216. As discussed above, magnetic inner cores 216 may comprise hard magnetic materials with high coercivity, such as $Fe_2O_3$, $CrO_2$, and Barium Ferrite BaFe. For example, magnetic inner cores 216 may comprise iron oxide based nanoparticle materials, including M $Fe_2O_4$ (where M may be Co, Ni, Cu, Zn, Cr, Ti, Ba, or Mg) nanomaterials, and iron oxide coated nanoparticle materials or other structures with similar functionality. As a result, in step 704, read sensor 108 may detect more than one type of nanoparticles 212 with a single sweep of the calibration assembly 100.

In step 706, the read response is stored. In one embodiment the read response is stored in the memory 640. In step 708 the processor 502 then increments the sample count. In step 710 the processor 502 determines if the sample count is less than a sample count threshold. The sample count threshold is defined as the number of read response samples necessary for determining a correlation signal profile. The sample count threshold may be preconfigured by the manufacturer or defined by the user or other administrator.

If it is determined in step 710 that the number of sample counts is less than the sample count threshold, the process returns to step 702. In step 702 the head module 104 with at least one magneto-resistive read sensor 108 is swept along the y-axis of the calibration assembly 100 at another known nanoparticle 212 location (e.g. at nanoparticle 212B location shown at $y_2$ in FIG. 3C). If it is determined that the number of sample counts is not less than the sample count threshold the process flows to step 712 in which the process determines the correlation signal profile from the stored read responses. In step 714 the determined correlation signal profile is stored. In one embodiment, the correlation signal profile is stored in memory 640. In another embodiment the correlation signal profile is stored in the matched filter 630.

Figure 8A:
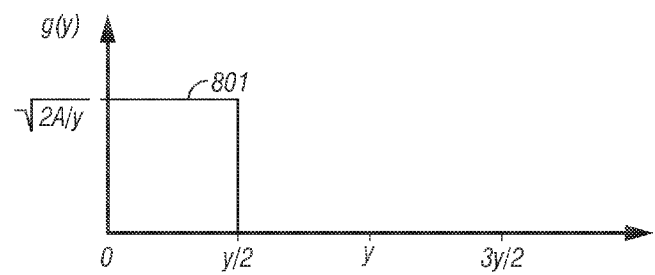
FIG. 8A illustrates the detection signal profile read by read sensor when a nanoparticle is detected in accordance with an embodiment of the invention.
Figure 8B:
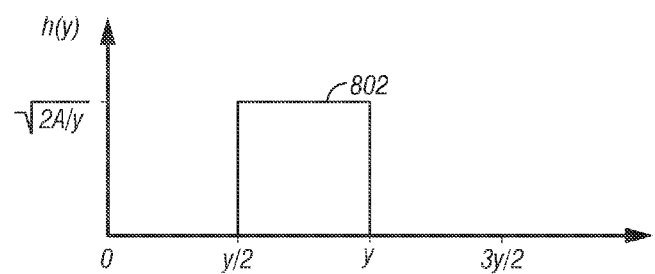
FIG. 8B illustrates the impulse response of an ideal signal profile of the detected nanoparticle in accordance with an embodiment of the invention.
Figure 8C:
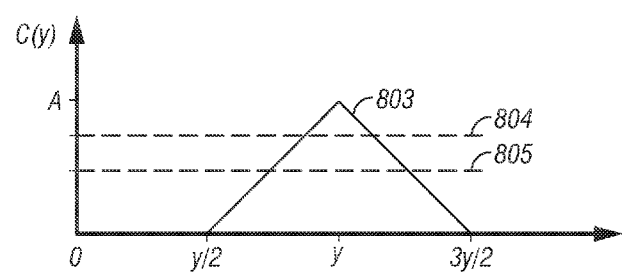
FIG. 8C illustrates the calculated correlation for the detection signal profile of each nanoparticle detected by read sensor in accordance with an embodiment of the invention.

FIGS. 8A, 8B and 8C illustrate the use of the correlation equation (Equation 1 above) to create an analog correlation C(y) 803 from signal 801 and matched filter 802 for the detection of a single nanoparticle 212. FIG. 8A illustrates the detection signal profile g(y) read by read sensor 108 when a nanoparticle 212 is detected. The variable A represents the amplitude of the signal 801 from the read sensor 108 when a nanoparticle 212 is detected by the read sensor 108. As discussed above, the magnetic read sensor 108 detects the magnetic properties of an inner core 216 based on the materials used for that inner core 216. Accordingly, nanoparticles 212 with different inner cores 216 will result in different detection signal profiles g(y).

FIG. 8B illustrates the impulse response h(y) of an ideal signal profile 802 of the detected nanoparticle 212. The impulse response h(y) of an ideal signal profile 802 may be stored in matched filter 630 for each nanoparticle.

FIG. 8C illustrates the calculated correlation C(y) 803 for the detection signal profile g(y) of each nanoparticle 212 detected by read sensor 108. The range of correlation C(y) is between −1 and +1, where +1 represents an ideal correlation of one hundred percent (100%), 0 indicates no correlation, and −1 indicates a completely reverse or opposite correlation.

In one embodiment, the manufacturer of the calibration assembly 100 defines a manufacturer's correlation threshold 804. The manufacturer's correlation threshold 804 is a threshold correlation value that the calibration assembly 100 must obtain during a calibration correlation test (further discussed with respect to FIGS. 10A and 10B below) to be deemed acceptable for calibration by the manufacturer. As discussed above, the range of correlation C(y) is between −1 and +1, where +1 represents an ideal correlation of one hundred percent (100%), 0 indicates no correlation, and −1 indicates a completely reverse, or opposite correlation. In one embodiment, the manufacturer's correlation threshold 804 is +0.8 such that the correlation is eighty percent (80%). However, it should be noted that the manufacturer's correlation threshold may be any level of correlation that the manufacturer deems is acceptable for their customers. For example, the manufacturer's correlation threshold may be in the range of +0.6 to +0.98 such that the correlation is between sixty and ninety-eight percent.

Further, in one embodiment the user of the calibration assembly 100 defines a user's correlation threshold 805. The user's correlation threshold 805 is a threshold correlation value that the calibration assembly 100 must obtain during a calibration correlation test (further discussed with respect to FIGS. 10A and 10B below) to be deemed acceptable by the user for calibration. In one embodiment, the user's correlation threshold 805 is +0.7 such that the correlation is seventy percent (70%). However, it should be noted that the user's correlation threshold may be any level of correlation that the user deems is acceptable for their application. For example, the user's correlation threshold in some embodiments may range between +0.4 and +0.95 such that the correlation is between forty and ninety-five percent. It should be noted that in most cases the manufacturer's correlation threshold is higher than that of the user because the manufacturer must meet each and every customer's user correlation thresholds.

As discussed above, the calibration trench 180 may have a plurality of nanoparticles (e.g. nanoparticles 212A, 212B, and 212C etc). Accordingly, Equation 2 expresses the correlation C(j) for a finite number of discrete digital pulses.

$$C(j) = \sum_{i=1}^{j} g(j)h(j-i) \quad \text{Equation 2}$$

Figure 9A:
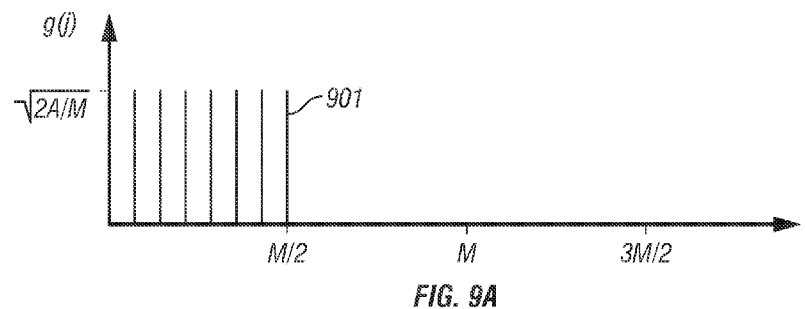
FIG. 9A illustrates the detection signal read by read sensor when multiple nanoparticles are detected in accordance with an embodiment of the invention.
Figure 9B:
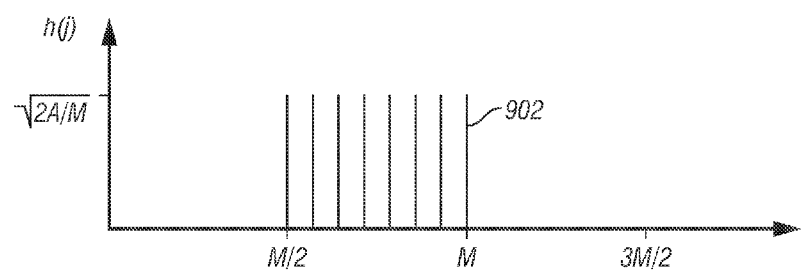
FIG. 9B illustrates the impulse response of the ideal signal profiles of multiple detected nanoparticles in accordance with an embodiment of the invention.
Figure 9C:
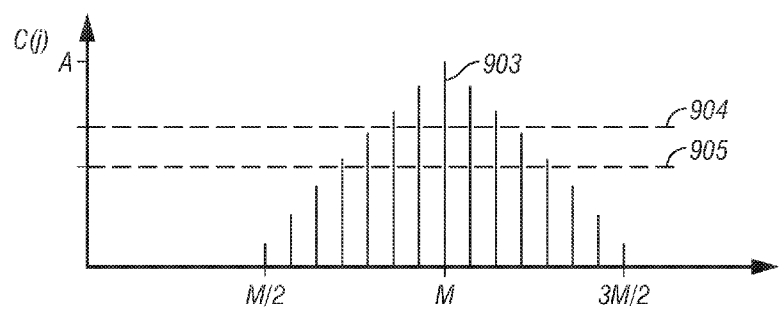
FIG. 9C illustrates the calculated correlation for the detected signal profiles of multiple detected nanoparticles by read sensor in accordance with an embodiment of the invention.

FIGS. 9A, 9B and 9C illustrate the use of the digital correlation equation (Equation 2) to create a digital correlation C(j) 903 from discrete digital pulses g(j) 901 and matched filter 902 for the detection of a finite number of discrete digital pulses from nanoparticles 212. For example, in one embodiment, in which there are eight (8) nanoparticles 212 positioned at known y-axis locations along the calibration trench 180 there are eight digital pulses. FIG. 9A illustrates the detection signal g(j) read by read sensor 108 when eight (8) nanoparticles are detected as shown by eight (8) digital pulses of signal 901. The variable A represents the amplitude of the signal 901 from the read sensor 108. Further, the variable M represents the number of pulses detected by read sensor 108. FIG. 9B illustrates the impulse response h(j) of the ideal signal profiles 902 of eight (8) detected nanoparticles 212. The impulse responses h(j) of an ideal signal profile 902 may be stored in matched filter 630. FIG. 9C illustrates the calculated correlation C(j) 903 for the detected signal profiles g(j) of the eight (8) detected nanoparticles 212 by read sensor 108.

In one embodiment the manufacturer of the calibration assembly 100 defines a manufacturer's correlation threshold 904. Again, the manufacturer's correlation threshold 904 is a threshold correlation value that the calibration assembly 100 must obtain during a calibration correlation test (further discussed with respect to FIGS. 10A and 10B below) to be deemed acceptable for calibration by the manufacturer. In one embodiment, the manufacturer's correlation threshold 804 is +0.8 such that the correlation is eighty percent (80%). However, it should be noted that the manufacturer's correlation threshold may be any level of correlation that the manufacturer deems is acceptable for their customers. For example, the manufacturer's correlation threshold may be in the range of +0.6 to +0.98 such that the correlation is between sixty and ninety-eight percent.

Further, in one embodiment the user of the calibration assembly 100 defines a user's correlation threshold 905. As discussed above, the user's correlation threshold 905 is a threshold correlation value that the calibration assembly 100 must obtain during a calibration correlation test (further discussed with respect to FIGS. 10A and 10B below) to be deemed acceptable by the user for calibration. In one embodiment, the user's correlation threshold 805 is +0.7 such that the correlation is seventy percent (70%). However, it should be noted that the user's correlation threshold may be any level of correlation that the user deems is acceptable for their application. For example, the user's correlation threshold in some embodiments may range between +0.4 and +0.95 such that the correlation is between forty and ninety-five percent. Again, it should be noted that in most cases the manufacturer's correlation threshold is higher than that of the user because the manufacturer must meet each and every customer's user correlation thresholds.

In one embodiment, processor 502 compares this calculated correlation C(y) against a stored correlation signal profile Co before accepting the signal g(y) as a valid detection of a nanoparticle 212.

Figure 10A:
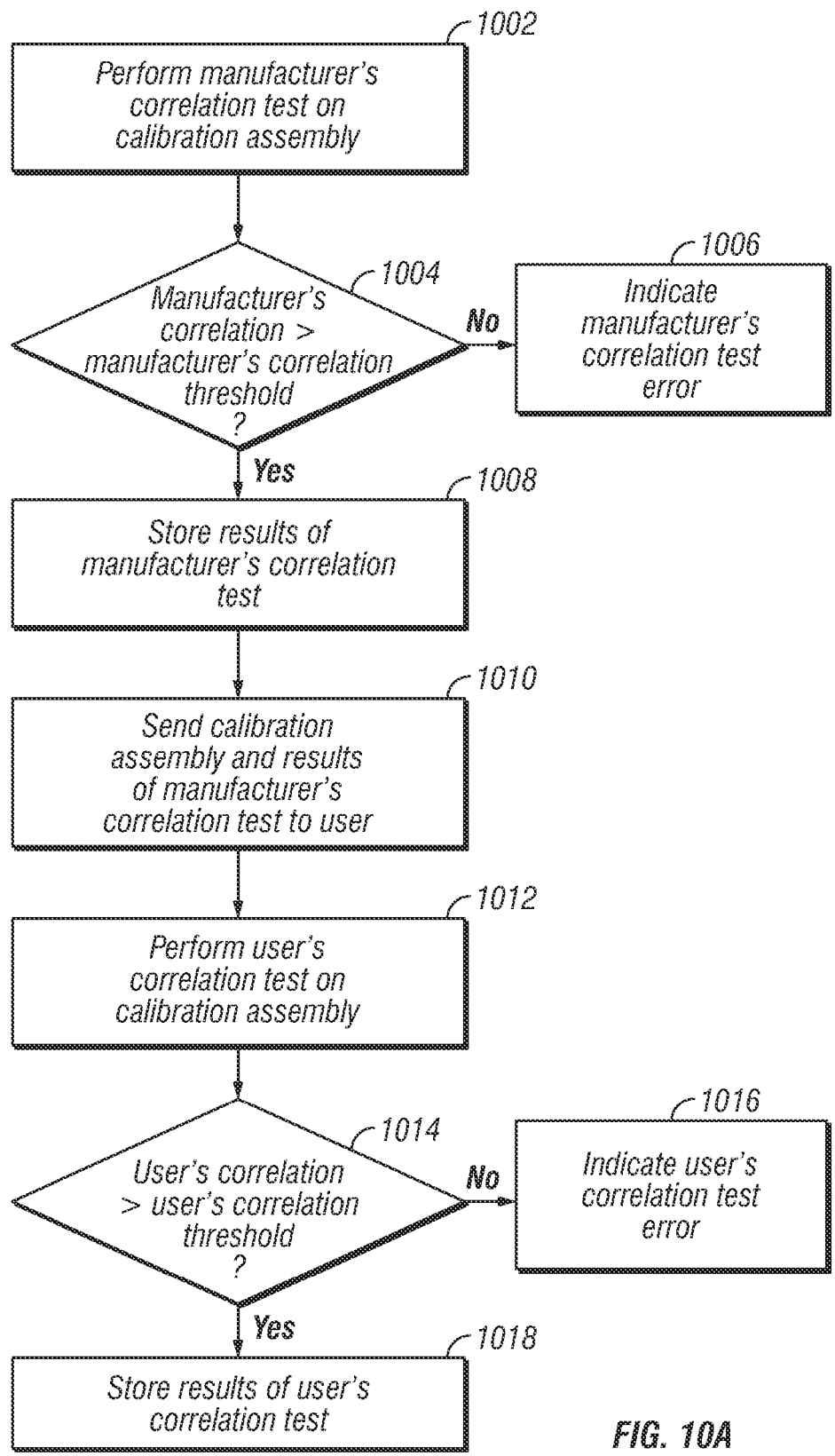
FIG. 10A is a flow chart illustrating the process of performing a calibration correlation test for a calibration assembly 100 in accordance with an embodiment of the invention.
Figure 10B:
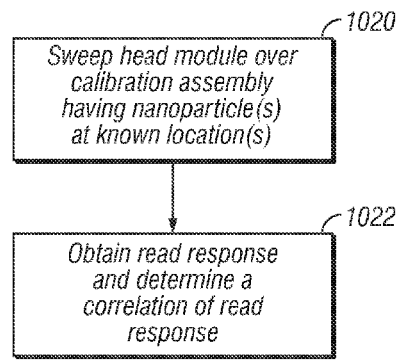
FIG. 10B is a flow chart illustrating further details of performing the correlation test on the calibration assembly in accordance with an embodiment of the invention.

In one embodiment, the ideal signal stored in the matched filter 630 of the write and read circuitry 600 is utilized in a manufacturer's and user's correlation test of a calibration assembly 100 to ensure that the calibration assembly is within the manufacturer's and user's acceptable standards for calibration of their write and read assemblies. FIG. 10A illustrates the process of performing a calibration correlation test for a calibration assembly 100. In one embodiment, the process begins with step 1002 in which a manufacturer's correlation test is performed on the calibration assembly. FIG. 10B provides further details of the steps of performing the manufacturer's correlation test on the calibration assembly 100. For example, in step 1020 of FIG. 10B the head module 104 with at least one magneto-resistive read sensor 108 is swept along the y-axis of the calibration assembly 100 at a known nanoparticle 212 location. For example, the head module 104 is swept along the y-axis of the calibration assembly 100 at location $y_1$ shown in FIG. 3C where it is known nanoparticle 212A is located. The magnetic properties of nanoparticle 212A are known. The process of sweeping head module over the calibration assembly 100 is the same process as described with respect to step 702 of FIG. 7 and is not repeated herein.

In step 1022 of FIG. 10B a read response is obtained for the nanoparticle 212A and the processor 502 determines a correlation of the read response. In an embodiment in which a single nanoparticle 212 is detected, the processor 502 utilizes Equation 1 to determine a correlation C(y) of the read response. In an embodiment in which a plurality of nanoparticles 212 are detected, the processor 502 utilizes Equation 2 to determine a correlation C(j) of the read response. The correlation C(y) or C(j) during the manufacturer's correlation test is referred to herein as the manufacturer's correlation.

Returning to step 1004 in FIG. 10A, the processor 502 determines if the manufacturer's correlation is greater than the manufacturer's correlation threshold 804 or 904. If the manufacturer's correlation is not greater than the manufacturer's correlation threshold 804 or 904 then the process proceeds to step 1006. In step 1006, if the correlation C(y) is at or below manufacturer's correlation threshold 804, or if correlation C(j) is at or below manufacturer's correlation threshold 904, then a manufacturer's correlation test error is indicated. In an embodiment in which a manufacturer's correlation test error is indicated the calibration assembly 100 may be rejected. A rejected calibration assembly 100 should not be utilized for calibration by the manufacturer or a user. In one embodiment, a rejected calibration assembly is destroyed. Alternatively, in one embodiment, one or more read sensors 108 of a head module 104 may be calibrated (as discussed further with respect to FIG. 13) in response to the indication of a manufacturer's correlation test error.

However, if the manufacturer's correlation is greater than the manufacturer's correlation threshold 804 or 904, then the calibration assembly 100 passed the manufacturer's correlation test. In step 1008 the results of the manufacturer's correlation test are stored in the memory 640 of processor 502. Alternatively, or in addition, the results of the manufacturer's correlation test are stored in the matched filter 630. A calibration assembly 100 that passes the manufacturer's correlation test indicates that the calibration assembly 100 is deemed acceptable by the manufacturer to be utilized for calibration by any user. Accordingly, the process proceeds to step 1010 in which the calibration assembly 100 and the results of the manufacturer's correlation test are sent to a user.

In step 1012 the user performs a user correlation test on the calibration assembly 1012. FIG. 10B provides further details of the steps of performing the user's correlation test on the calibration assembly 100. For example, in step 1020 of FIG. 10B the head module 104 with at least one magnetoresistive read sensor 108 is swept along the y-axis of the calibration assembly 100 at a known nanoparticle 212 location. For example, the head module 104 is swept along the y-axis of the calibration assembly 100 at location $y_1$ shown in FIG. 3C where it is known nanoparticle 212A is located. The magnetic properties of nanoparticle 212A are known. The process of sweeping head module over the calibration assembly 100 is the same process as described with respect to step 702 of FIG. 7 and is not repeated herein.

In step 1022 of FIG. 10B a read response is obtained for the nanoparticle 212A and the processor 502 determines a correlation of the read response. In an embodiment in which a single nanoparticle 212 is detected, the processor 502 utilizes Equation 1 to determine a correlation C(y) of the read response. In an embodiment in which a plurality of nanoparticles 212 are detected, the processor 502 utilizes Equation 2 to determine a correlation C(j) of the read response. The correlation C(y) or C(j) during the user's correlation test is referred to herein as the user's correlation.

Returning to step 1014 in FIG. 10A, the processor 502 determines if the user's correlation is greater than the user's correlation threshold 805 or 905. If the user's correlation is not greater than the user's correlation threshold 805 or 905 then the process proceeds to step 1016. In step 1016 if the correlation C(y) is at or below user's correlation threshold 805, or if correlation C(j) is at or below user's correlation threshold 905 then a user's correlation test error is indicated. In an embodiment in which a user's correlation test error is indicated the calibration assembly 100 may be rejected. A rejected calibration assembly 100 should not be utilized for calibration by the user. In one embodiment, a rejected calibration assembly is destroyed. Alternatively, in one embodiment, the read sensor 108 may be calibrated (as discussed further with respect to FIG. 13) in response to the indication of a user's correlation test error.

However, if the user's correlation is greater than the user's correlation threshold 805 or 905, then the calibration assembly 100 passed the user's correlation test. In step 1018 the results of the user's correlation test are stored in the memory 640 of processor 502. Alternatively, or in addition, the results of the user's correlation test are stored in the matched filter 630. A calibration assembly 100 that passes the user's correlation test indicates that the calibration assembly 100 is deemed acceptable by the user to be utilized for calibration by that user.

Magnetic sensors, such as GMR sensors, contain magnetic materials whose combined effect is to have a resistance change when subjected to a magnetic field. When subjected to low-level electrical overstress (EOS) or electrostatic discharge (ESD) current/voltage pulses the GMR sensors can be damaged or degraded. Still further, corrosion or other aging processes can damage magnetic sensors over time, reducing the signal strength and possibly leading to failure. In one embodiment, a method of determine if a read sensor is damaged or degraded is described. Still further, if it is determined that a read sensor is degraded, a method of calibrating a read sensor is described. Calibration of each individual read sensor allows for uniform read responses from each read sensor on a read head and prevents unreliable and inaccurate detection of analytes due to degradation. If a read sensor 108 is degraded sufficiently by mild corrosion or ESD/EOS events, then it's ability to detect an analyte or to discriminate between the number of analytes may be jeopardized. Therefore, having a means to determine the response of the read sensor 108 in situ is important for proper use of the read sensor 108.

The read sensor 108 described above may include a GMR stack. U.S. Patent Application No. 2009/0268325, entitled "METHODS FOR DETECTING DAMAGE TO MAGNETORESISTIVE SENSORS," is hereby incorporated by reference in its entirety for its showing of magnetoresistive sensors.

Figure 11:
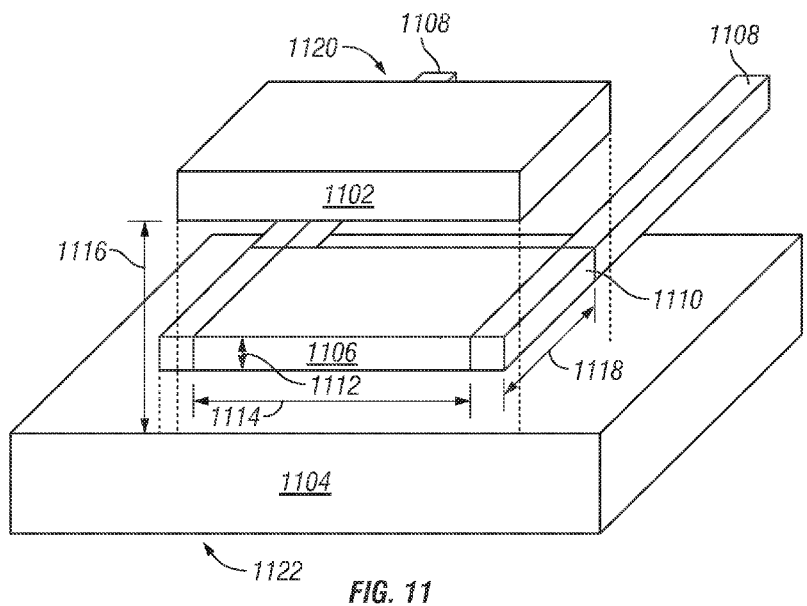
FIG. 11 is a schematic diagram of a current-in-plane (CIP) read-sensor which may be used in conjunction with various embodiments of the invention.

FIG. 11 is a schematic diagram of a current-in-plane (CIP) read-sensor which may be used in conjunction with various embodiments, including the embodiment of read sensor 108. The sensor stripe 1106 is between a first shield 1104 and a second shield 1102. The sensor stripe 1106 has multiple layers but is here depicted as a single sheet. Leads 1108 extend from the sensor stripe 1106 so that an electrical connection can be made. The sensor stripe 1106 has dimensions of width 1114, thickness 1112, and height 1118. Also, the there typically is a gap 1116 between the first shield 1104 and second shield 1102. The sensor stripe may have a hard bias magnet 1110 on either edge of the sensor stripe 1106 toward the leads 1108. Below the first shield 1104 is the undercoat 1122, and above the second shield 1102 is an overcoat 1120.

Figure 12A:
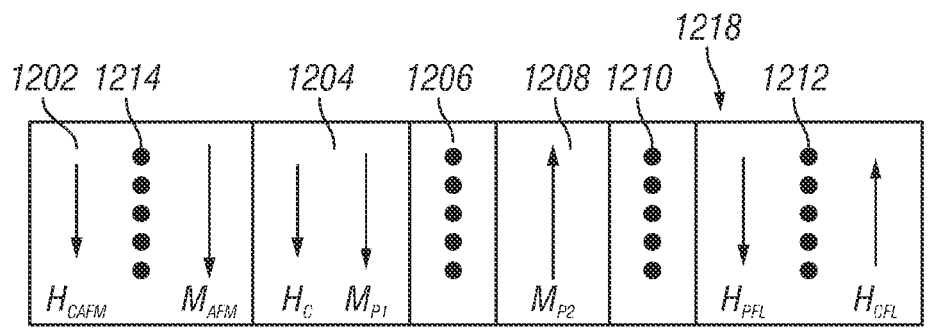
FIG. 12A shows a schematic diagram of the current flow through a GMR stack and the associated magnetic fields as viewed along a slice in the stack when a forward (positive) bias current is applied in accordance with an embodiment of the invention.
Figure 12B:
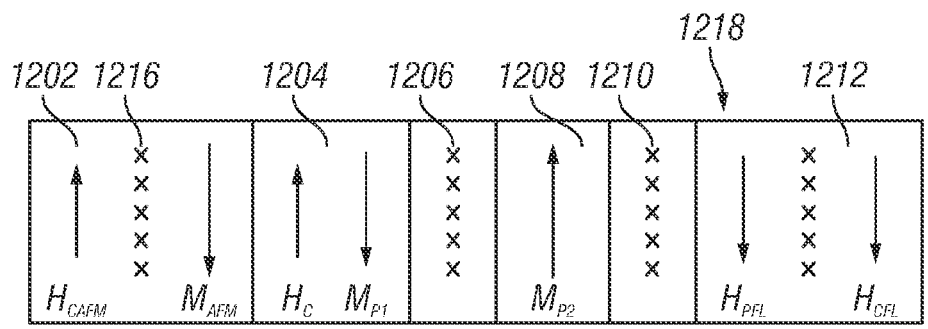
FIG. 12B is a schematic diagram of the current flow through a GMR stack and the associated magnetic fields as viewed along a slice in the stack when a reverse (negative) bias current is applied in accordance with an embodiment of the invention.
Figure 12C:
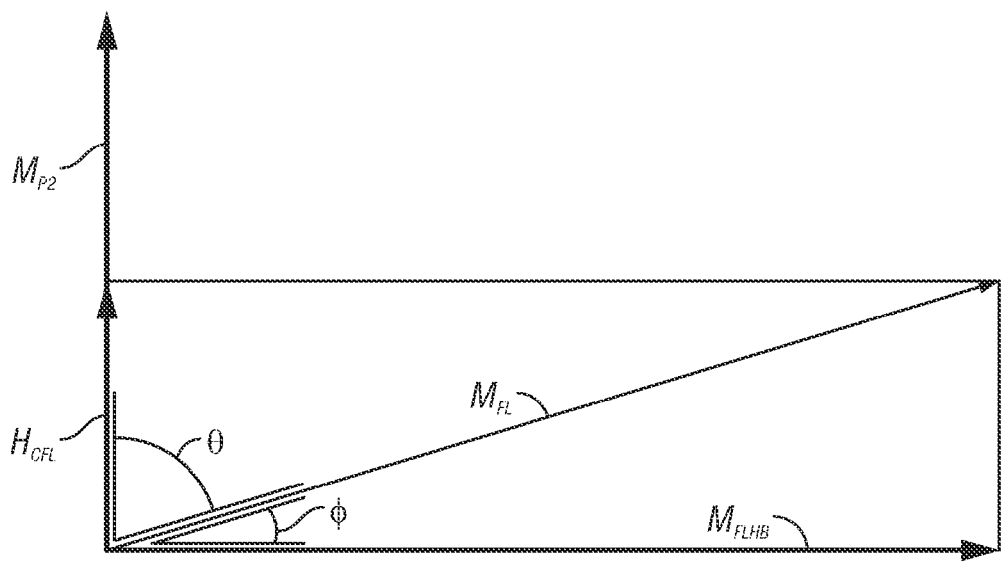
FIG. 12C is a schematic diagram of the net magnetization inside the free layer of a generic GMR stack.

FIGS. 12A, 12B, and 12C can now be used to more fully understand the following descriptions of several embodiments.

FIG. 12A shows a schematic diagram of the current flow through a generic GMR stack and the associated magnetic fields as viewed along a slice in the stack when a forward (positive) bias current is applied. It should be noted that a bias current is simply a current passed through the sensor, and no special characteristics or requirements should be attributed to the bias currents described herein unless otherwise noted. The vertical axes are in the stripe height orientation and the horizontal axes are in the stripe thickness orientation. The track width is into the page and the sample-bearing surface 1218 is at the top of the figure. The darkened circle represents current flow 1214 out of the page. The magnetic field in the antiferromagnet (AFM) layer 1202 at the interface with the adjacent ferromagnetic layer 1204 is represented by $M_{AFM}$ on FIG. 12A and is assumed to be vertical. $M_{AFM}$ could be the net field in the AFM or the field at the interface of the first pinned layer ($PL_1$). $M_{AFM}$ forces the magnetization ($M_{P1}$) in the first pinned layer 1204 to also be in the vertical direction. The spacer layer 1206 separates the second pinned ferromagnetic layer 1208 from the pinned layer 1204, and the proper thickness and coupling between the pinned layer 1204 and the second pinned ferromagnetic layer ($PL_2$) 1208 results in the magnetization in the second pinned ferromagnetic layer 1208 ($M_{P2}$) to be reverse-aligned with $M_{P1}$. The layers described create a synthetic antiferromagnet (SAFM). A copper layer 1210 separates the SAFM from the free layer (FL) 1212. The combination of magnetizations in the SAFM creates a magnetization ($H_{PFL}$) in the free layer 1212, which is arbitrarily shown in the vertical orientation in FIG. 12A. The bias current flow ($I_{mr}$) in the stack generates a magnetic field in the AFM layer 1202 of $H_{CAFM}$ and in the free layer 1212 of $H_{CFL}$. For forward bias current flow 1214, $H_{CAFM}$ is aligned with $M_{AFM}$ and the magnetization of the first pinned layer 1204 ($H_C$) is aligned with $M_{P1}$, and aligned with $M_{P2}$. $H_{CFL}$ is reverse-aligned with $H_{PFL}$.

FIG. 12B is a schematic diagram of the current flow through a generic GMR stack and the associated magnetic fields as viewed along a slice in the stack when a reverse (negative) bias current is applied. It should be noted that a bias current is simply a current passed through the sensor, and no special characteristics or requirements should be attributed to the bias currents described herein unless otherwise noted. All the definitions from FIG. 12A apply here, and instead of darkened circles, FIG. 12B has x's which indicate reverse bias current flow 1216, which is into the page. The combination of magnetizations in the SAFM creates a magnetization ($H_{PFL}$) in the free layer 1212, which is arbitrarily shown in the vertical orientation in FIG. 12B. The bias current flow ($I_{mr}$) in the stack generates a magnetic field in the AFM layer 1202 of $H_{CAFM}$ and in the free layer 1212 of $H_{CFL}$. For reverse bias current flow 1216, $H_{CAFM}$ is reverse-aligned with $M_{AFM}$, $H_C$ is reverse-aligned with $M_{P1}$, and $H_{CFL}$ is aligned with $H_{PFL}$.

FIG. 12C is a schematic diagram of the net magnetization ($M_{FL}$) inside the free layer (1212 of FIG. 12A) for a forward biased sensor stripe formed by the vector sum of the magnetizations from the hard bias magnets ($M_{FLHB}$) and the free layer magnetization $H_{CFL}$. Also shown is the orientation of the magnetization $M_{P2}$ is the second pinned layer (408 in FIG. 12A).

To first order, the change in resistance of the GMR sensor due to the GMR effect varies as the cosine of the angle between the magnetization in the $PL_2$ and the FL. For the design described above, and shown in FIGS. 12A, 12B and 12C, due to the GMR effect, the reverse bias currents result in a slightly higher sensor resistance as compared with the sensor resistance for forward bias currents of the same magnitude. One of ordinary skill in the art would understand that if the design included a reverse of the magnetization of $PL_2$ (and thus of $PL_1$), the converse would be true.

Returning to FIG. 11, the GMR read sensor includes leads 1108 and a hard bias magnet 1110 which are connected to the sensor stripe 1106. The sensor stripes 1106 are made from stacks of metals deposited on a wafer in a rectangular sheet (stripe) which has a width W, height H, and a sheet resistance ($R_{sheet}$). The resistance is given by Equations 3A and 3B:

$$R_{mro} = R_{total} - R_{lead} \qquad \text{Equation 3A}$$

$$R_{mro} = R_{sheet} \frac{W}{H} \qquad \text{Equation 3B}$$

Equation 3A gives the sensor stripe resistance ($R_{mr}$), which is determined by subtracting the lead-hard-bias resistance ($R_{lead}$) from the total measured resistance ($R_{total}$). Equation 3B gives the MR stripe resistance ($R_{mro}$) at ambient temperature and low bias current in terms of $R_{sheet}$ and the rectangular properties of the stripe. The fabrication process includes polishing (lapping) a smooth head-bearing-surface (HBS), which results in a given value of H for each sensor, which usually has a wide tolerance range for manufactured parts. H, then can be determined from the measured value of $R_{mro}$ using the known values of W and $R_{sheet}$ with Equation 3B.

Two main physical parameters which affect the GMR stripe resistance are magnetic field and temperature, both of which are affected by the current ($I_{mr}$) passing through the sensor stripe 1106. External magnetic fields impinging on the sensor stripe 1106 will also affect the stripe resistance, as will be discussed below.

Since the current passing through the thin sensor also heats the sensor up due to Joule heating and the positive change in resistance with temperature, the combined effects of heating and the GMR effect from the magnetic field generated by the bias current must be taken into account. As will be shown later, for a given current, the difference in the resistance measured with forward and reverse bias currents are, to first order, related to the GMR effect, while the sum of the two resistances is dominated by the Joule heating effect.

The effect of temperature and magnetic field on the stripe resistance ($R_{mr}$) is given, to first order, by the following equations:

$$R_{mr}(\Delta T_{mr}) = R_{mro}[1 + \alpha_{mr} * \Delta T_{mr}] - \delta_{gmr}(\Delta T_{mr})\cos(\theta)] \qquad \text{Equation 4A}$$

$$\delta_{gmr}(\Delta T_{mr}) = \delta_{gmro}[1 - \Delta T_{mr}/T_C]^{0.5} \qquad \text{Equation 4B}$$

The first term in Equation 4A is the standard temperature dependence of the stripe resistance, with $\alpha_{mr}$ measured to be in the range of about 0.001 to about 0.002° $C.^{-1}$ for extant GMR sensors, and $R_{sheet}$ is on the order of 10 to 25 Ω/sq. $\Delta T_{mr}$ is the temperature rise above ambient temperature (e.g., about 25° C.). The second term in Equation 4B is the GMR component to the resistance with $\delta_{gmr}(\Delta T_{mr})$ being the temperature dependent fractional GMR resistance when the pinned layer ($M_{PL}$) and the free layer ($M_{FL}$) magnetizations are anti-parallel, and θ (from FIG. 12C) is the angle between $M_{P2}$ and $M_{FL}$ (θ=π/2+φ in FIG. 12C). Equation 4B gives a phenomenological formula for the temperature dependence of $\delta_{gmr}(\Delta T_{mr})$. Extant GMR sensors have a $\delta_{gmro}$ nominally of around 5 to 15% at room temperature ($\Delta T_{mr}$=0). In Equation 3D, $T_C$ is a temperature, which experimentally is determined to be in the range of about 425° C. to 500° C. for a given sensor. H and W are the stripe height 1118 and the track width 1114 as indicated in FIG. 11.

In normal operation, $M_{P2}$ and $M_{FL}$ are designed to be almost perpendicular. The deviation from perpendicularity is due to the rotation of $M_{FL}$ by $M_{P1}$ ($\phi_{PL}$) and the magnetic field generated by the bias current ($H_{CFL}$). It should be noted that a bias current is simply a current passed through the sensor, and no special characteristics or requirements should be attributed to the bias currents described herein unless otherwise noted. A current $I_{mr}$ will generate a magnetic field $H_{CFL}$ within the free layer, which to first order is given by Equation 5.

$$H_{CFL} = \frac{\mu_0 f I_{mr}}{2H} \quad \text{Equation 5}$$

where $\mu_0$ is the permeability of free space, and H is the stripe height of the read sensor 108, and f is a factor less than unity. The cosine of the angle $\theta$, $\cos(\theta)$, is then proportional to $H_{CFL}$, and is given by Equation 6.

$$\cos(\theta) \equiv \epsilon I_{mr}. \quad \text{Equation 6}$$

The stripe temperature rise versus bias current ($I_{mr}$) is assumed to be proportional to the power in the stripe:

$$\Delta T_{mr} = \frac{R_{mr}(\Delta T_{mr}) I_{mr}^2}{\kappa_{mr}} \quad \text{Equation 7}$$

$\kappa_{mr}$, termed the thermal conductance, completely defines the sensor Joule heating. Combining Equation 3A through Equation 7 yields the following.

$$\Delta T_{mr} = \frac{[\gamma_{mr}/\alpha_{mr}] I_{mr}^2 [1 - \epsilon \delta_{gmr} I_{mr}]}{1 - \gamma_{mr} I_{mr}^2} \quad \text{Equation 8A}$$

$$R_{mr}(I_{mr}) = \frac{R_{mr0}[1 - \epsilon \delta_{gmr} I_{mr}]}{1 - \gamma_{mr} I_{mr}^2} \quad \text{Equation 8B}$$

Where, $$\gamma_{mr} = \frac{\alpha_{mr} R_{mr}(I_{mr} \geq 0)}{\kappa_{mr}} \quad \text{Equation 8C}$$

Since $\delta_{gmr}$ is a function of temperature, in Equations 8A and 8B, $\delta_{gmr}$ is a function of $I_{mr}$. For small currents, $\delta_{gmr}$ can be treated as a constant. For higher currents, with large temperature changes, Equations 8A-8B must be solved numerically.

Accordingly, it can be shown that:

$$R_{pnl}(I_{mr}) = \frac{R_{mr}(I_{mr}) - R_{mr}(-I_{mr})}{2 I_{mr} R_{mr}(I_{mr})} \approx \epsilon \delta_{gmr} \quad \text{Equation 9A}$$

A constant, K, can be defined as:

$$K = \epsilon \delta_{gmr} \quad \text{Equation 9B}$$

where $I_{mr}$ is the applied forward bias current and where $-I_{mr}$ is the reverse applied bias current, and is K is a calibration constant. Note that while c should be a constant for a given design and geometry, $\delta_{gmr}$, and thus K, will vary slightly for individual sensors. Factors which affect $\delta_{gmr}$ include, among others: stresses, process variations within a wafer, post-wafer processing variations, corrosion, and EOS/ESD damage.

The purpose of a GMR sensor is to detect external magnetic fields. Knowing the strength of those fields yields important information. The application of an external field of $+H_{field}$ will result in a change in resistance given by:

$$R_{mr}(H_{field}) = R_{mr}(I_{mr})[1 + \beta \delta_{gmr} H_{field}] \quad \text{Equation 10}$$

Measuring the GMR resistance at both $+H_{field}$ and $-H_{field}$ results in a GMR response ($\Delta R_{mr}$) of:

$$\Delta R_{mr}(H_{field}) = R_{mr}(H_{field}) - R_{mr}(-H_{field}) \quad \text{Equation 11A}$$

$$\Delta R_{mr}(H_{field}) = 2\beta \delta_{gmr} H_{field} R_{mr}(I_{mr}) = J H_{field} R_{mr}(I_{mr}) \quad \text{Equation 11B}$$

where $$J = 2\beta \delta_{gmr} \quad \text{Equation 11B}$$

Both constants K and J are linearly proportional to $\delta_{gmr}$, where the proportionality are constants of the sensor geometry and other factors. If the sensors are damaged or age in the field, it is $\delta_{gmr}$ which should change, so the ratio of K/J should remain constant. Thus, initial values of both K ($K_o$) and J ($J_o$) may be determined for the read sensor 108 at the factory. $J_o$ may be determined at the factory by read sensor 108 manufacturer by exposing the read sensor 108 to a known external magnetic field. $K_o$ may also be determined at the factory measuring the sensor resistance for at least one pair of bias currents ($\pm I_{mr}$) and using Equation 9A.

The read response of a read sensor 108 to an internal field $H_{field}$ may be expressed as:

$$\Delta R_{mr}(H_{field}) = J H_{field} R_{mr}(I_{mr}) \quad \text{Equation 12A}$$

with $$J = K \frac{J_0}{K_0} \quad \text{Equation 12B}$$

Solving for $H_{field}$ gives:

$$H_{field} = \frac{1}{K} \frac{K_0}{J_0} \left[ \frac{\Delta R_{mr}(H_{field})}{R_{mr}(I_{mr})} \right] \quad \text{Equation 12C}$$

As discussed above, the value of the calibration constant, K, can be measured by the user using Equations 9A and 9B above, and the initial values of the calibration constants K and J which are expressed as $K_o$ and $J_o$ respectively, may be determined by the manufacturer. Therefore, for a set bias current $I_{mr}$, and with a read sensor 108 having a measure resistance of $R_{mr}$, and a change in resistance of $\Delta R_{mr}$ when the read sensor 108 is swept across a nanoparticle 212, the calibrated magnetic field $H_{field}$ may be calculated based on Equation 12C.

Further, the manufacturer may define a range of acceptable values of the initial calibration constant $K_0$ for a given read sensor 108. For example, the manufacturer may define a minimum acceptable value for the initial calibration constant, $K_{0min}$. In addition the manufacturer may define a maximum acceptable value for the initial calibration constant, $K_{0max}$. In one embodiment, a manufacturer's defined acceptable calibration constant range is defined, such that $K_{0min} < K_0 < K_{0max}$. If it is determined that the value of the initial calibration constant $K_0$ for a read sensor 108 is not within the manufacturer's defined acceptable calibration constant range the read sensor 108 is repaired or replaced.

It is important to note that the value of the calibration constant K may change with time. For example, the read sensor 108 may degrade over time due to low-level electrical overstress (EOS) or electrostatic discharge (ESD) events. Therefore, the user may define a range of acceptable values of the calibration constant K for a given read sensor 108. For example, the user may define a minimum acceptable value for the calibration constant, $K_{umin}$. In addition the user may define a maximum acceptable value for the calibration constant, $K_{umax}$. In one embodiment, a user's defined acceptable calibration constant range is defined, such that $K_{umin}<K<K_{umax}$. If it is determined that the value of the calibration constant K for a read sensor 108 is not within the user's defined acceptable calibration constant range the read sensor 108 is repaired or replaced. However, if it is determined that the value of the calibration constant K for a read sensor 108 is within the user's defined acceptable calibration constant range then read sensor 108 is calibrated. In one embodiment the user may define an acceptable calibration constant range of $0.5<K/K_o<1.5$.

Figure 13:
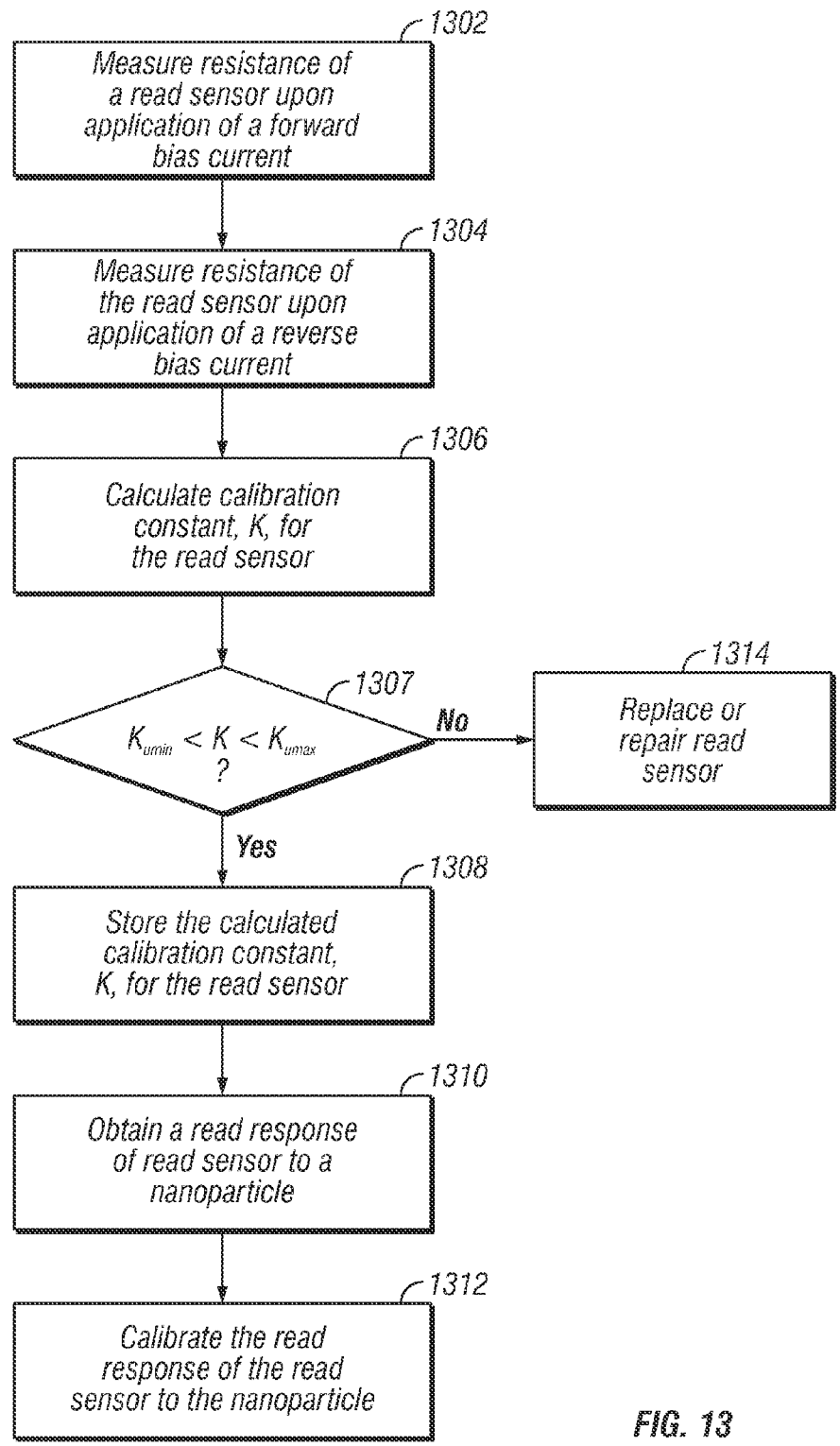
FIG. 13 illustrates a process of calibrating a read sensor of the head module in accordance with an embodiment of the invention.

FIG. 13 illustrates a process of calibrating a read sensor 108 of the head module 108. In step 1302 the processor 502 measures the resistance of the read sensor 108 upon an application of a forward bias current. In step 1304 the processor 502 measures the resistance of the read sensor 108 upon application of a reverse bias current. In one embodiment, the forward bias current and the reverse bias current have the same magnitude. In step 1306 the processor 502 calculates the calibration constant for the read sensor 108. In one embodiment, the processor 502 calculates the calibration constant K for the read sensor 108 utilizing Equation 9A as discussed above.

In another embodiment, the resistance of the read sensor 108 is measured at several bias currents, including forward and reverse bias currents. Specifically, a plurality of first resistances are measured at a plurality forward bias currents and a plurality of second resistances are measured at corresponding reverse bias currents. For example resistance values may be measured at 1, 2, 3, 4 and 5 mA. Herein, the plurality of resistances measured at forward bias currents are collectively referred to as a plurality of first resistances. Similarly, a plurality of second resistances are measured at corresponding reverse bias currents. For example, resistances may be measured at bias currents of −1, −2, −3, −4 and −5 mA. Herein, the plurality of resistances measured at reverse bias currents are collectively referred to as a plurality of second resistances. Accordingly, the calibration constant, K is determined based on the plurality of first measured resistances and the plurality of the second measured resistances such that:

$$K = \sum \frac{R_{pnl}(I_{mr})}{N_m} \quad \text{Equation 13}$$

Where the $\Sigma$ indicates the sum over the measured $I_{mr}$, and $N_m$ is the number of measurements. Accordingly, for $I_{mr}$ of 1, 2, 3, 4 and 5 mA, $N_m$ would be 5.

One of ordinary skill in the art would understand, that while an example of five first and second plurality of resistances are described, any number of plurality of first and second resistances could be measured at their corresponding bias currents.

In step 1307, the processor determines if the calibration constant is within the user defined acceptable calibration constant range (i.e. is $K_{umin}<K<K_{umax}$) If it is determined that the calibration constant K is not within the user defined acceptable calibration constant range then the process flows to step 1314. In step 1314 the read sensor 108 is determined unacceptable and the read sensor 108 is repaired or replaced.

However, if in step 1307 it is determined that the calibration constant K is within the user defined acceptable calibration constant range, such that $K_{umin}<K<K_{umax}$, then the process flows to step 1308. In step 1308 the calibration constant is stored. In one embodiment the calibration constant is stored in the processor 502. Further, in one embodiment, the calibration constant is stored in memory 640 of the processor 502.

In step 1310, a read response of the read sensor 108 to a nanoparticle. The read response may be obtained by sweeping a head module over a calibration assembly or any sample assembly having nanoparticles obtained thereon. For example, the read response may be obtained as described in FIG. 10B of the instant application by sweeping the read sensor 108 over a calibration assembly or by the step of sweeping the read sensor over sample assembly described with respect to FIG. 4 of copending and coassigned U.S. patent application Ser. No. 12/970,837 entitled "TRENCHED SAMPLE ASSEMBLY FOR DETECTION OF ANALYTES WITH ELECTROMAGNETIC READ-WRITE HEADS," which is incorporated by reference.

In step 1312 the read response obtained in step 1310 is calibrated based on the calibration constant K calculated in step 1306 utilizing Equations 12A, 12B and 12C. For example, for a set bias current $I_{mr}$, and with the read sensor 108 having a measured resistance of $R_{mr}$, and a change in resistance of $\Delta R_{mr}$ when the read sensor is swept across a nanoparticle 212, the calibrated magnetic field $H_{field}$ is be calculated based on Equation 12C.

Calibration of each individual read sensor in this manner allows for uniform read responses from each of the read sensors 108 on a read head 104, and prevents unreliable an inaccurate detection of analytes due to sensor degradation or differences in sensor responses.

The terms "certain embodiments", "an embodiment", "embodiment", "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries. Additionally, a description of an embodiment with several components in communication with each other does not imply that all such components are required. On the contrary a variety of optional components are described to illustrate the wide variety of possible embodiments.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously, in parallel, or concurrently.

While particular embodiments of the present invention have been shown and described, it will be obvious to those skilled in the art that, based upon the teachings herein changes and modification may be made without departing form this invention and its broader aspects and, therefore, the appended claims are to encompass within their scope all such changes and modifications as are within the true spirit and scope of this invention. Furthermore, it is to be understood that the invention is solely defined by the appended claims.

What is claimed is:

1. A calibration assembly comprising:
    an outer layer having at least one calibration trench extending along a y-axis; and
    an encapsulation layer within said calibration trench, said encapsulation layer having a plurality of nanoparticles spaced apart along said y-axis of said at least one calibration trench,
    wherein each of said plurality of nanoparticles are provided at known y-axis locations within said calibration trench, and
    wherein each of said plurality of nanoparticles have a known magnetic property.

2. The calibration assembly of claim 1, further comprising magnetic servo alignment marks.

3. The calibration assembly of claim 2, wherein said calibration assembly further comprises a servo alignment trench in said outer layer, said servo alignment trench parallel with said calibration trench.

4. The calibration assembly of claim 1, wherein said outer layer is selected from the group consisting of diamond-like-carbon, polytetrafluoroethylene aluminum oxide, and polyamides.

5. The calibration assembly of claim 1, wherein said calibration assembly further comprises a base layer and wherein said base layer is selected from the group consisting of gold, silicon, and silicon oxide.

6. A calibration assembly comprising:
    an outer layer having at least one calibration trench extending along a y-axis; and
    an encapsulation layer within said calibration trench, said encapsulation layer having a plurality of nanoparticles spaced apart along said y-axis of said at least one calibration trench,
    wherein each of said plurality of nanoparticles are encapsulated within said encapsulation layer,
    wherein each of said plurality of nanoparticles are provided at known y-axis locations in said calibration trench, and
    wherein each of said plurality of nanoparticles have a known magnetic property.

7. The calibration assembly of claim 6, further comprising magnetic servo alignment marks.

8. The calibration assembly of claim 7, wherein said calibration assembly further comprises a servo alignment trench in said outer layer, said servo alignment trench parallel with said calibration trench.

9. The calibration assembly of claim 6, wherein said outer layer is selected from the group consisting of diamond-like-carbon, polytetrafluoroethylene aluminum oxide, and polyamides.

10. The calibration assembly of claim 6, wherein said calibration assembly further comprises a base layer and wherein said base layer is selected from the group consisting of gold, silicon, and silicon oxide.

11. A calibration assembly comprising:
    an outer layer having at least one calibration trench extending along a y-axis; and
    an encapsulation layer within said calibration trench, said encapsulation layer having a plurality of nanoparticles spaced apart along said y-axis of said at least one calibration trench,
    wherein said encapsulation layer comprising a cured polymer resin and each of said plurality of nanoparticles being encapsulated within said cured polymer resin,
    wherein each of said plurality of nanoparticles are provided at known y-axis locations in said calibration trench, and
    wherein each of said plurality of nanoparticles have a known magnetic property.

12. The calibration assembly of claim 11, further comprising magnetic servo alignment marks.

13. The calibration assembly of claim 12, wherein said calibration assembly further comprises a servo alignment trench in said outer layer, said servo alignment trench parallel with said calibration trench.

14. The calibration assembly of claim 11, wherein said outer layer is selected from the group consisting of diamond-like-carbon, polytetrafluoroethylene aluminum oxide, and polyamides.

15. The calibration assembly of claim 11, wherein said calibration assembly further comprises a base layer and wherein said base layer is selected from the group consisting of gold, silicon, and silicon oxide.

* * * * *